United States Patent
Santos et al.

(10) Patent No.: US 11,564,816 B2
(45) Date of Patent: Jan. 31, 2023

(54) RADIALLY RIGID AND LONGITUDINALLY FLEXIBLE MULTI-ELEMENT INTRAVASCULAR STENT

(71) Applicant: EFEMORAL MEDICAL LLC, Los Altos, CA (US)

(72) Inventors: Jayson Delos Santos, Fremont, CA (US); Christopher Haig, Los Altos, CA (US); Lewis B Schwartz, Lake Forest, IL (US)

(73) Assignee: EFEMORAL MEDICAL, INC., Los Altos, CA (US)

( * ) Notice: Subject to any disclaimer, the term of this patent is extended or adjusted under 35 U.S.C. 154(b) by 802 days.

(21) Appl. No.: 16/340,248

(22) PCT Filed: Oct. 7, 2016

(86) PCT No.: PCT/US2016/055953
§ 371 (c)(1),
(2) Date: Apr. 8, 2019

(87) PCT Pub. No.: WO2018/067171
PCT Pub. Date: Apr. 12, 2018

(65) Prior Publication Data
US 2020/0038206 A1    Feb. 6, 2020

(51) Int. Cl.
*A61F 2/82* (2013.01)
*A61F 2/958* (2013.01)
(Continued)

(52) U.S. Cl.
CPC .............. *A61F 2/82* (2013.01); *A61F 2/958* (2013.01); *A61L 31/022* (2013.01); *A61L 31/041* (2013.01); *A61F 2/9522* (2020.05); *A61F 2002/826* (2013.01); *A61F 2002/91575* (2013.01); *A61F 2230/0017* (2013.01); *A61F 2240/001* (2013.01); *A61F 2250/0067* (2013.01)

(58) Field of Classification Search
CPC .......... A61F 2/82; A61F 2/958; A61F 2/9522; A61F 2002/826; A61F 2002/91575;
(Continued)

(56) References Cited

U.S. PATENT DOCUMENTS 6,187,034 B1 * 2/2001 Frantzen .................... A61F 2/91
623/1.11
9,254,212 B2 * 2/2016 Papp ...................... A61F 2/915
(Continued)

FOREIGN PATENT DOCUMENTS

WO    2016141215 A1    9/2016

OTHER PUBLICATIONS

International Search Report and Written Opinion for Application No. PCT/US2016/055953, dated Dec. 29, 2016, 7 pages.
(Continued)

*Primary Examiner* — Christopher M Koehler
(74) *Attorney, Agent, or Firm* — Convergence Intellectual Property Law P.C.; Jonathan Garfinkel

(57) ABSTRACT

A multi-element, vascular stent may be used to maintain or enhance patency of a blood vessel. The stent may be used in peripheral blood vessels, which may be long and/or tortuous. By using multiple, separate stent elements that are balloon expandable, the multi-element stent may be stronger than a traditional self-expanding stent but may also be more flexible, due to its multiple-element configuration, than a traditional balloon-expandable stent. The distance between stent elements may be based on characteristics of the stent and the target vessel location such that the stent elements do not touch one another during skeletal movement. Thus, the multi-element, vascular stent described herein may be particularly advantageous for treating long lesions in tortuous peripheral blood vessels.

12 Claims, 27 Drawing Sheets

(51) Int. Cl.
*A61L 31/02* (2006.01)
*A61L 31/04* (2006.01)
A61F 2/915 (2013.01)
A61F 2/95 (2013.01)

(58) Field of Classification Search
CPC ........ A61F 2230/0017; A61F 2240/001; A61F 2250/0067; A61L 31/022; A61L 31/041
See application file for complete search history.

(56) References Cited

U.S. PATENT DOCUMENTS

| | | |
|---|---|---|
| 9,585,779 B2 * | 3/2017 | Papp ................ B29C 65/64 |
| 2008/0154351 A1 * | 6/2008 | Leewood .............. A61F 2/89 |
| | | 606/139 |
| 2008/0234798 A1 | 9/2008 | Chew et al. |
| 2011/0152997 A1 | 6/2011 | Kelly et al. |
| 2013/0268045 A1 * | 10/2013 | Papp ................ A61F 2/966 |
| | | 623/1.11 |

OTHER PUBLICATIONS

Smouse H.B., et al., "Biomechanical Forces in the Femoropopliteal Arterial Segment," Endovascular Today, Jun. 2005 (online), Retrieved from URL: http://evtoday.com/2005/06/EVT0605_F3_Smouse. html, on Dec. 1, 2016, entire document.
International Preliminary Report on Patentability Chapter I for Application No. PCT/US2016/055953, dated Apr. 9, 2019, 6 pages.

* cited by examiner

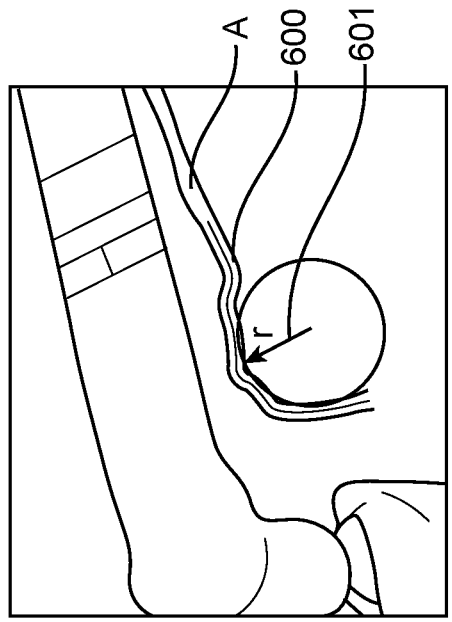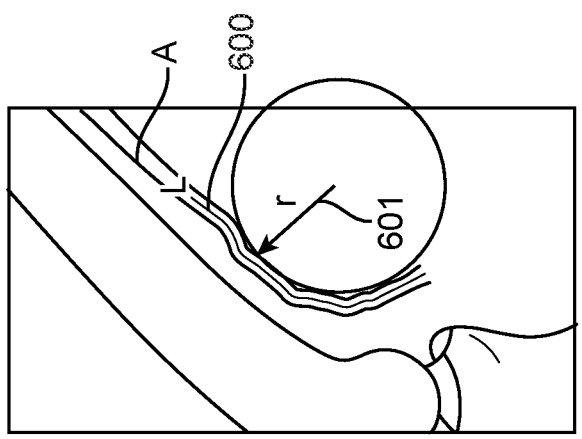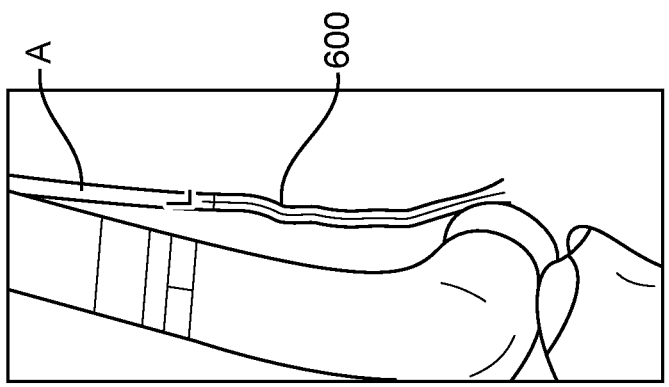

RADIALLY RIGID AND LONGITUDINALLY FLEXIBLE MULTI-ELEMENT INTRAVASCULAR STENT

FIELD OF THE INVENTION

The present application pertains generally to the field of medical devices. More specifically, the present application pertains to the design and manufacture of intravascular stents intended to maintain patency (blood flow) of blood vessels (arteries and veins).

BACKGROUND

Atherosclerotic cardiovascular disease is the leading cause of death and disability in the world, accounting for nearly one-third of all human mortality. Atherosclerosis is the pathologic process of arterial aging; over time, the once soft and pliable arteries become stiff and brittle, then fouled by the development of fatty, cholesterol plaques. As cholesterol plaques grow large enough reduce the flow of blood and oxygen to vital organs, they cause the clinical syndromes of chest pain (angina pectoris), gangrene (critical limb ischemia) and transient ischemic attack (mini-stroke). Plaques that are unstable, laden with complex calcification and blood clot, can abruptly rupture and occlude the arteries in which they reside. These generate the acute clinical events of heart attack (myocardial infarction), acute arterial ischemia and stroke.

Atherosclerotic cardiovascular disease is an international epidemic. Although many developed nations have made significant strides in risk factor modification, the worldwide prevalence of atherosclerotic disease is still increasing. Globally, an estimated 16.7 million deaths were attributed to atherosclerosis in 2010 and projections suggest an increase to 23.3 million by the year 2030. The economic cost is staggering. In the United States alone, the estimated direct and indirect cost of heart disease in 2010 was $204.4 billion.

For decades, the only available treatment for occlusive atherosclerotic plaques in arteries was surgical bypass grafting. In 1977, a new method was introduced in which plaques could be internally stretched and cracked by intraluminal balloons advanced over coaxial wires. The development of so-called "percutaneous transluminal coronary balloon angioplasty" (PTCA) ushered in a new, non-surgical era of therapy for arterial occlusive disease. The field was further advanced through the development of intracoronary metal stents which were shown to yield superior patency results to balloon angioplasty alone.

Since their introduction in the 1980's, intravascular stents have changed radically. Through refinements in engineering, metallurgy and manufacturing, modern stents exhibit increasing better flexibility, trackability, radial strength, conformability, rheology, biocompatibility and radiopacity. Two major designs categories have emerged: balloon-expandable stents (BES) and self-expanding stents (SES). While both types are intended to increase and maintain the flow channel of diseased arteries, they perform this function in radically different ways.

Balloon-Expandable Stents (BES)

The first stent type to be widely applied to the treatment of atherosclerotic plaques was a balloon-expandable stents (BES) designed as an open mesh tube comprised of stainless steel. When crimped onto an angioplasty balloon it could be advanced through the arterial tree coaxially and deployed directly within the plaque. Stent implantation created a larger and more durable flow channel as compared to balloon angioplasty alone.

In the modern era, balloon-expandable stents are deployed in virtually every case of percutaneous coronary intervention (PCI) and in about half of all peripheral interventional procedures.

FIG. 1 shows a force analysis of a balloon-expandable stent inflated in a 7 mm target vessel. During balloon inflation, the stent contacts the vessel when it reaches 7 mm signified by symbol (a). Balloon, artery and stent are inflated together to 9 mm, reaching point (b). This generates a tension force within the artery, approximately 0.13 N/mm in the figure. When the balloon is deflated, the tension force within the artery re-compresses the stent until equal to its radial resistive force, point (c). The difference in diameter between points (b) and (c) is referred to as the stent recoil.

As the arterial lumen is always larger than the diameter of the crimped stent, the initial balloon and stent expansion occurs without contact to the arterial wall. When the expanding stent initially contacts the wall (signified by symbol (a)), the stretched artery begins to exert an opposing inward force on the expanding balloon and stent. Maximum inflation (determined by the operator) is illustrated by point (b) in the figure. It is generally maintained for 1-3 minutes in an attempt to relax the stretched artery. When the balloon is finally deflated and withdrawn, the tension generated within the expanded artery partially re-compresses the stent until an equilibrium is reached between the inwardly-directed arterial tension of the artery and the outward radial resistive force of the stent. The difference between the stent diameter at maximum balloon inflation and the stent diameter following balloon withdrawal is commonly referred to as the stent recoil.

BES are rigid and non-deformable medical devices; they are deployed by inflating their delivery balloon within the target lesion and embedding the rigid scaffold within the vessel wall. The final stent shape is casted by the deformation produced by the balloon, and held in place by the opposing collapsing force of the target artery. Its architecture is permanent; reimaging the device over time generally reveals no change in the diameter or shape that was achieved during the procedure.

In order to fulfill these design inputs, BES are rigid medical devices. They typically maintain their cylindrical shape under pressures of 15.8-28.9 N/cm. These are non-physiologic forces that far exceed any vascular pressure observed within the human body; in fact, BES are more than ten times more rigid than the vessels they inhabit. Because they are so rigid, BES can only be implanted in a limited number of anatomic locations, namely those with minimal or highly predictable motion such as the coronary arteries, renal arteries and common iliac arteries. Due to their inherent lack of flexibility, BES are absolutely contraindicated in a number of important peripheral vascular beds including the carotid, subclavian, external iliac, common femoral, superficial femoral and popliteal arteries.

The rigidity of BES also severely limits their usable length. BES that are too long will damage or kink arteries that bend, leading to restenosis, thrombosis, pseudoaneurysm formation and, in some cases, device fracture and migration. Knowing their dangers, stent manufacturers make their devices available in only limited lengths. Although atherosclerotic lesions in peripheral arteries can be several hundred cm long, the longest available BES is only 60 mm.

Self-Expanding Stents (SES)

As early as 1969, it was theorized that intravascular stents should be flexible rather than rigid. First developed for aerospace applications, an equiatomic alloy made of nickel-titanium called nitinol was thought to exemplify the ideal mechanical properties for the scaffolding of blood vessels. One property was superelasticity, or the ability of a metal to return to its original shape after a substantial deformation. This assured flexibility within arteries in motion and the ability to reform the arterial lumen following its temporary collapse by extremity flexion. The other was shape memory, or the ability of an alloy to be annealed at one temperature, substantially deformed at a lower temperature, then return to its original shape when heated to its original temperature. This enabled the development of intravascular, tubular nitinol self-expanding stents (SES). They are created by laser cutting nitinol tubes at body temperature (37° C.) then deforming the tubes when cooled to enable loading into delivery systems. When the device is ultimately deployed in a blood vessel at body temperature, it expands to assume its original, annealed shape.

The first self-expanding nitinol stent to be approved for clinical use was a simple, coiled wire made of nitinol. It was introduced into the American market in 1992. Seamless tubes of nitinol became available shortly thereafter, enabling the development of laser-cut, tubular nitinol stents. In the modern era, tubular, nitinol SES are the most common devices deployed in long, flexible blood vessels such as the external iliac and superficial femoral arteries.

The forces generated by the intravascular deployment of SES are vastly different from BES. SES are much gentler and expand vessels much less completely than BES. FIG. 2 shows a force analysis of a self-expanding stent inflated in a 7 mm target vessel. The stent is deployed from its delivery system until it contacts with the vessel wall at point (a). Both vessel and stent expand to point (b); at this point the outforce of the stent has reached an equilibrium with the compressive force of the vessel. The operator removes the SES delivery system and replaces it with an 8.5 mm angioplasty balloon in an attempt to further expand the device and vessel. The balloon is expanded to 8.5 mm at point (c) then deflated and removed. The act of further expanding the stented vessel increases its diameter to >8 mm (d).

By design, they deform easily, at pressures ranging from only 0.39-1.7 N/cm (29-128 mmHg). Therefore, in order to get them to expand more fully, SES are routinely post-dilated with balloons following their deployment. Even after repeated balloon dilatation, however, the relatively weak SES often cannot fully expand the diseased, recoiling artery.

The result is an insufficient post-procedure diameter and intraoperative outcome. This is a frequent occurrence with SES, especially in peripheral arteries with significant burdens of atherosclerosis disease. In one study, underexpansion of the target lesion (defined as >30% residual stenosis) was observed in 70% of cases after SES implantation. In some cases, the only available treatment is to implant the stronger BES inside the weaker SES.

The second drawback of the use of SES is their disquieting tendency toward fracture. Only occasionally observed after balloon-expanding stenting, SES fracture is alarmingly common, as high as 65% in one clinical report. Although not fully understood, one attractive hypothesis for this phenomenon is that fracture may be a function of the unique biomechanical forces exerted on stents dwelling in the SFA. Movement of the legs is a complex motion; loading of the hips and knees during ambulation repeatedly compresses the arteries axially and can even produce multidimensional bends, twists and kinks. Because the stent isn't rigid and moves in tandem with the artery, the repeated deformation can result is single or multiple strut fractures or, in severe cases, complete stent transection. Not surprisingly, SES fracture is more common after implantation of long and/or overlapping stents and in more active patients. Fracture of intravascular stents is clearly associated with restenosis, although it remains controversial whether the relationship is associative or causal.

Lastly, unlike the relatively transient forces imparted by BES, the unique mechanism and design of SES unfortunately assures that a continuous, chronic outward force will be applied to the treated artery. Stenting with BES causes an initial perturbation as the artery is stretched. Once deployed, however, BES are rigid so the forces are static. In contrast, vessels that contain a SES are continually subjected to interaction with a foreign body as well as the chronic outward forces (COF) exerted by the device. These forces are generated because SES must be "oversized" when implanted; in order to assure that the SES doesn't migrate following deployment, the manufacturer's nominal diameter of the stent must exceed the target lesion's reference vessel diameter (RVD). Because the final diameter of the device is, by definition, less than its nominal shape memory diameter, the stent will exert an outward stretching force upon the wall of the vessel until such time that its nominal diameter is reached (if ever). Considering the motion of the vessels in which these devices are typically implanted, SESs exert continual and chronic perturbations upon the vessel walls that they contact. This explains the relatively poor long-term patency of arteries treated with SES, indeed, restenosis complicates roughly 40% of all peripheral vascular interventions after one year. This led a recent international consensus panel of cardiologists, vascular surgeons and interventional radiologists to suggest that the current state-of-the-art of SFA stenting results in only about 60% primary patency over the first year and continues to decline over the long-term.

Summary of Differences Between BES and SES

The fact that BES and SES are both intended to treat atherosclerotic arteries is, essentially, their only similarity. The two devices differ in virtually every other respect: material, design, pattern, method of manufacture, mode of delivery and vascular response. An illustration of their differences is shown in FIG. 3 which depicts side-by-side how the forces generated by BES and SES vary with their diameter.

Expanded BES are rigid; they can resist forces as high 5 N/mm; forces which are rarely, if ever, reached within the human body. They have no shape memory; if deformed, they will remain deformed and pose a continual threat to arterial patency. In contrast, SES generate much less force within the vessel; so little that they often fail to achieve full expansion of the target lesion. They exhibit a high degree of shape memory, however, so will return to their fully expanded state if transiently deformed by arterial movement or compression.

Not surprisingly, the two stent types also generate vastly different cellular responses within blood vessels. At first blush, it might be assumed that the vasculature would exhibit a more rigorous inflammatory and hypercellular response to the stiff, non-physiologic BES as opposed to the more gentle SES. This is not the case, however. The trauma of BES implantation does induce inflammation and vascular smooth muscle cell (VSMC) activation, but the response tends to be transient and, because the applied forces equilibrate and the stent is motionless, self-limited. In this respect, the vascular response to a BES is similar to that of any motionless foreign body within human beings. There is an initial inflammatory reaction followed by fibrosis and scarring intended to separate or wall off the invading antigen.

The 30-day response of experimental arteries treated with BES has been a surprisingly consistent finding. It parallels the clinical observation that, once stable for several months, bare metal stents implanted in the human coronary, renal and common iliac arteries generally enjoy long-term patency.

In contrast, the vascular response to SES implantation tends to be more severe. Because the stent exhibits relatively little radial force, it cannot be dilated and embedded into the lesion similar to BES. Instead, it must be oversized relative to the vessel wall such that its nominal (manufactured) diameter exceeds the target lesion's reference vessel diameter (RVD). This is the only way to assure that the device will stay in place once deployed within the dynamic arterial system.

SES oversizing assures that all devices will be deployed in a partially compressed state. Given the stents' inherent self-expanding design, it will continue to exert a chronic outward force upon the vessel wall until such time that the device finally achieve its nominal diameter (if ever). As the gentle stent rarely can exert enough force to fully expand itself, the COF may persist for the life of the patient. It is a fundamentally different kind of foreign body, one that continues to move, press, disturb and interact with its host.

The net reaction is dependent on both the degree of oversizing and the dwell time of the device. In cases of severe oversizing in arteries that exhibit repetitive movement with skeletal muscle, the reaction can be profound. In an attempt to adapt and exclude the foreign body, the artery will completely fill its lumen with SMCs and fibrin, rendering the artery useless as a conduit for blood flow.

In summary, BES are the preferred device for endovascular treatment of occlusive lesions in the arterial tree. They are mechanically inert so induce only a transient pathologic response from which the arterial readily and reliably heals. Their only disadvantage is that their rigidity precludes implantation in long arteries that require the flexibility to accommodate skeletal movement.

Therefore, it would be advantageous to have a stent for use in peripheral vasculature that is easier to design, develop and manufacture than currently available stents. Ideally, such a stent would have a desirable flexibility and conformability profile while also having sufficient strength to withstand the stresses placed on peripheral vascular stents, as described above. This would make the stent more useful and effective, and safe for the treatment of long, tortuous blood vessels. At least some of these objectives will be met by the embodiments described below.

SUMMARY

The embodiments herein describe an apparatus for maintaining the luminal integrity of long, naturally moveable and flexible human blood vessels by simultaneous deployment of multiple independent, repeating, rigid scaffold units. The embodiments may include multiple, rigid, repeating units that are closely spaced within the vessel but do not touch one another, even when skeletal movement or myocardial contraction causes the vessel to move.

In some embodiments, a stent may include multiple, rigid, potentially articulating elements, which are simultaneously implanted along the length of a vessel via balloon inflation. Each element of the stent may have relatively high radial force (rigidity), similar or greater in magnitude to that of traditional, balloon-expandable stents. Each element may also be relatively short and rigid, so that its nominal diameter will be reached immediately upon balloon inflation, and thus it will not exert chronic forces upon the vessel. Additionally, because each element is relatively short in length, each may move independently, in concert with the artery into which it is implanted. In this way, such a stent may be used safely in any vessel of the body, regardless of the vessel's length, proximity to joints or range of motion.

In one aspect, a method for manufacturing an intravascular stent may comprise loading a multi-element stent comprising multiple individual stent elements onto an inflatable balloon such that the stent elements are positioned serially along a longitudinal length of the balloon and the stent elements do not touch one another. Stent elements are spaced such that the stent elements do not touch one another at a target vessel location during skeletal movement. The stent is configured to be radially rigid and longitudinally flexible after implantation at the target vessel location.

The distance between each stent element may be based on a diameter of the stent element in an expanded state at a target vessel location and an angle created between stent elements during maximal flexion of the target vessel location during skeletal movement. In an embodiment, the distance between each stent element is based on a cosine of the angle created between stent elements during maximal flexion of the target vessel location during skeletal movement. In an embodiment, the distance between each stent element increases with an increased diameter of the stent element in the expanded state at the target vessel location. The distance between each stent element may be further based on a length of the stent elements. In an embodiment, the distance between each stent element increases with increased length of the stent elements. The distance between each stent element may be further based on a number of elements in the multi-element stent. In an embodiment, the distance between each stent element decreases with increased number of elements in the multi-element stent. The distance between each stent element may be further based on a maximum percent axial compression of the stent elements at the target vessel location. In an embodiment, the distance between each stent element increases with an increase of the maximum percent axial compression of the stent elements at the target vessel location.

In certain embodiment, the stent elements are equal in length. The multi-element stent may be comprised of more than two stent elements. In such embodiment, the distances between each stent element may be equal. Each of the stent elements may separated by a distance of at least half a millimeter while mounted on the balloon and after implantation.

In some embodiments, the stent may be formed from a material comprising poly(L-lactic acid) (PLLA), poly(D-lactic acid) (PDLA), poly(D,L-lactic acid) (PDLLA), semicrystalline polylactide, polyglycolic acid (PGA), poly (lactic-co-glycolic acid) (PLGA), poly(iodinated desamino tyrosyl-tyrosine ethyl ester) carbonate, polycaprolactone (PCL), salicylate based polymer, polydioxanone (PDS), poly(hydroxybutyrate), poly(hydroxybutyrate-co-valerate), polyorthoester, polyanhydride, poly(glycolic acid-co-trimethylene carbonate), poly(iodinated desaminotyrosyl-tyrosine ethyl ester) carbonate, polyphosphoester, polyphosphoester urethane, poly(amino acids), cyanoacrylates, poly (trimethylene carbonate), poly(iminocarbonate), polyalkylene oxalates, polyphosphazenes, polyiminocarbonates, and aliphatic polycarbonates, fibrin, fibrinogen, cellulose, starch, collagen, polyurethane including polycarbonate urethanes, polyethylene, polyethylene terephthalate, ethylene vinyl acetate, ethylene vinyl alcohol, silicone including polysiloxanes and substituted polysiloxanes, polyethylene oxide, polybutylene terephthalate-co-PEG, PCL-co-PEG, PLA-co-PEG, PLLA-co-PCL, polyacrylates, polyvinyl pyrrolidone, polyacrylamide, or combinations thereof. The selected material may be extruded into a cylindrical tubing. In other embodiments, the stent may be formed from a material comprising magnesium, stainless steel, platinum chromium, or cobalt chromium. The tubing may be laser cut with a pattern to form a stent element. In an embodiment, the stent elements are coated with an anti-proliferative agent.

The stent elements may comprise a plurality of diamond shaped closed cells longer in a longitudinal direction than in a radial direction when in an unexpanded state. In an embodiment, the stent elements comprise a plurality of diamond shaped closed cells longer in a radial direction than in a longitudinal direction in the expanded state. The distance between each stent element in an unexpanded state may be less than or equal to each stent element in the expanded state.

This and other aspects of the present disclosure are described herein.

BRIEF DESCRIPTION OF THE DRAWINGS

Present embodiments have other advantages and features which will be more readily apparent from the following detailed description and the appended claims, when taken in conjunction with the accompanying drawings, in which:

In FIG. 5A a multi-element stent mounted on a balloon is advanced to the lesion.

FIGS. 6A-6C are side views of a self-expanding Nitinol stent placed in a distal SFA and popliteal artery, illustrated during different amounts of leg flexion.

DETAILED DESCRIPTION

Figure 1:
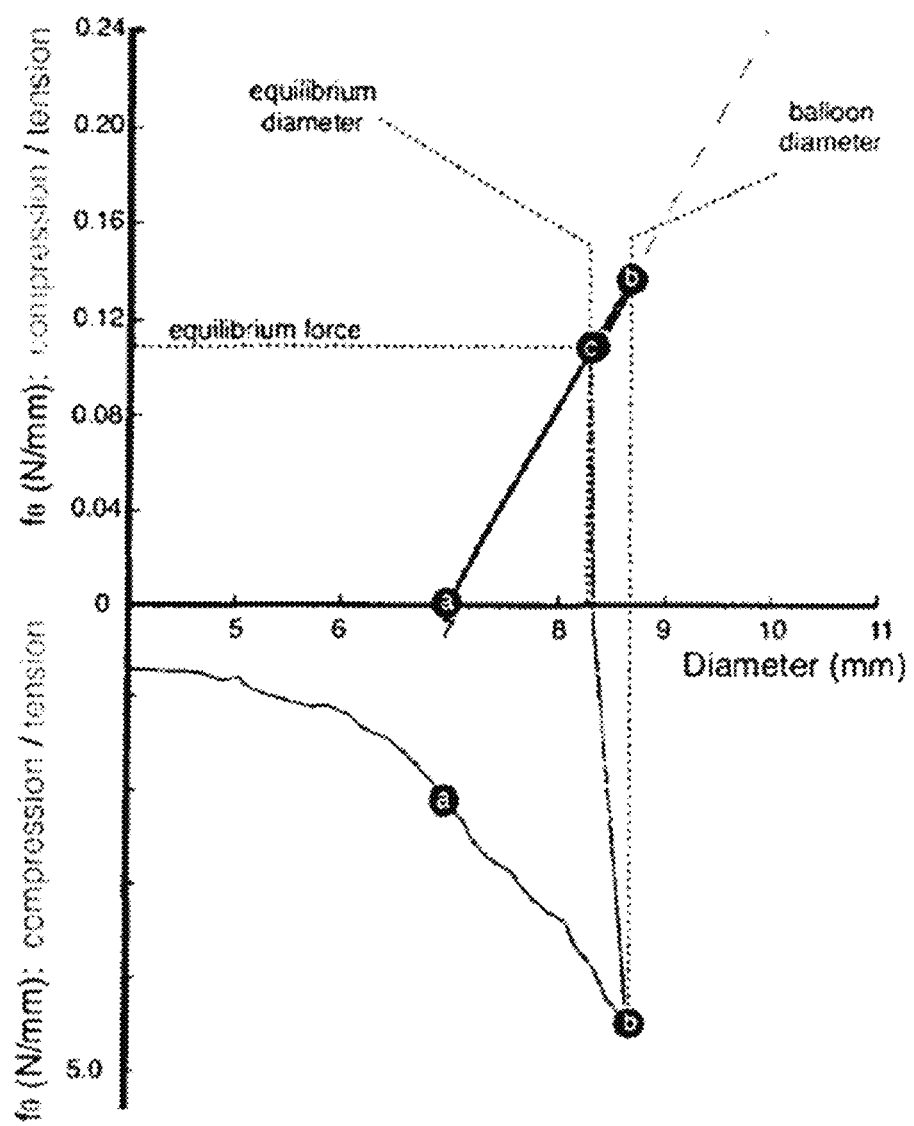
FIG. 1 shows a force analysis of a balloon-expandable stent inflated in a 7 mm target vessel.
Figure 2:
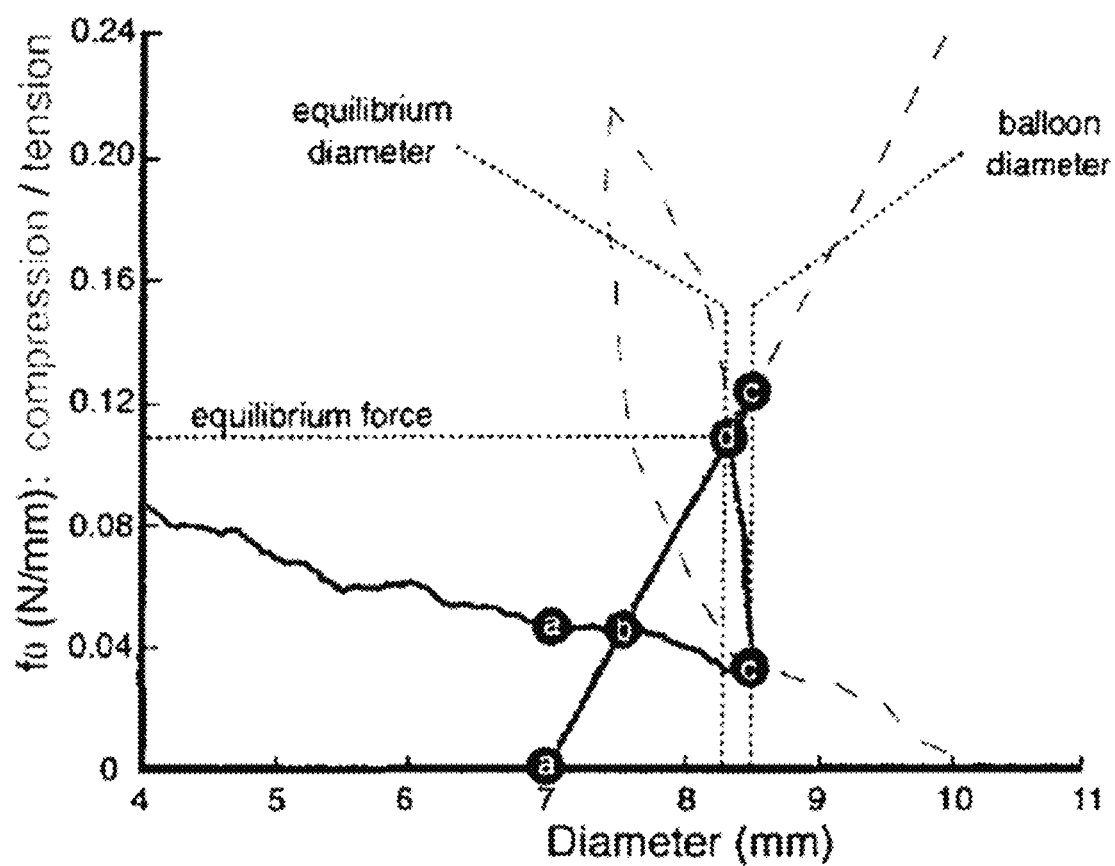
FIG. 2 shows a force analysis of a self-expanding stent inflated in a 7 mm target vessel.
Figure 3:
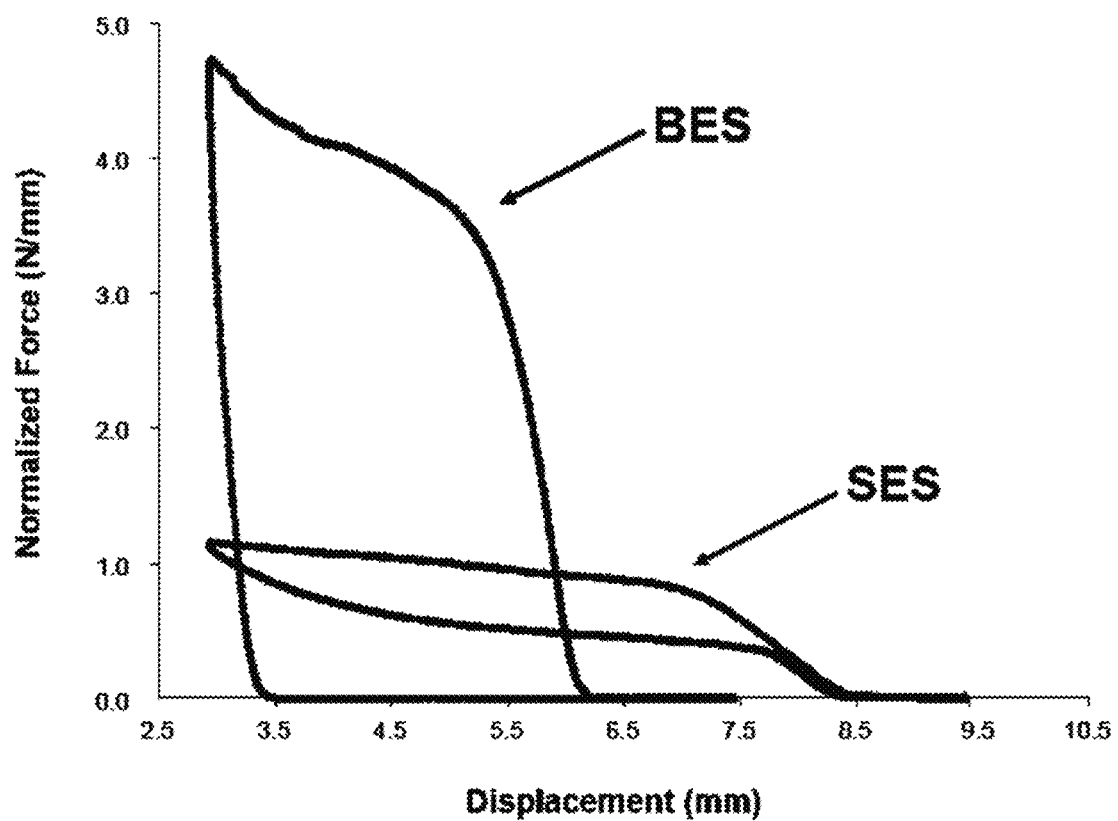
FIG. 3 depicts side-by-side how the forces generated by BES and SES vary with their diameter.

While the invention has been disclosed with reference to certain embodiments, it will be understood by those skilled in the art that various changes may be made and equivalents may be substituted without departing from the scope of the invention. In addition, many modifications may be made to adapt to a particular situation or material to the teachings of the invention without departing from its scope.

Throughout the specification and claims, the following terms take the meanings explicitly associated herein unless the context clearly dictates otherwise. The meaning of "a", "an", and "the" include plural references. The meaning of "in" includes "in" and "on." Referring to the drawings, like numbers indicate like parts throughout the views. Additionally, a reference to the singular includes a reference to the plural unless otherwise stated or inconsistent with the disclosure herein.

The word "exemplary" is used herein to mean "serving as an example, instance, or illustration." Any implementation described herein as "exemplary" is not necessarily to be construed as advantageous over other implementations.

Various embodiments are described herein with reference to the figures. The figures are not drawn to scale and are only intended to facilitate the description of the embodiments. They are not intended as an exhaustive description of the invention or as a limitation on the scope of the invention. In addition, an illustrated embodiment needs not have all the aspects or advantages shown. An aspect or an advantage described in conjunction with a particular embodiment is not necessarily limited to that embodiment and can be practiced in any other embodiments even if not so illustrated.

The embodiments herein describe the design of intravascular devices that maintain the flow channel (patency) of long, pliable blood vessels by providing rigid radial support while still maintaining axial flexibility. Traditionally, intravascular devices intended for use in long blood vessels had to be designed with relatively weak radial strength in order to maintain flexibility and accommodate the bending of the vessel required for organismal motion. The relative weakness of these traditional intravascular devices limits their ability to durably maintain an effective and sufficient channel for flowing blood.

In contrast, the devices described herein are multi-element, vascular stents (or "vascular scaffolds"). These stents are comprised of multiple, short, rigid, cylindrical stent segments, or elements, which are separate from one another but may be referred to together as a multi-element stent.

Generally, each element of the multi-element stents described herein will be sufficiently rigid to provide a desired level of strength to withstand the stresses of the vessel in which they are placed, such as a tortuous peripheral vessel. At the same time, a multi element stent will also be flexible, due to the fact that it is made up of multiple separate elements, thus allowing for placement within a curved, torturous blood vessel.

Additionally, the multi element stents described herein will usually be balloon-expandable rather than self-expanding, since balloon-expandable stents are typically stronger than self-expanding stents. Each balloon expandable element of the stent may have relatively high radial force (rigidity) due to the described structures and materials. A stent element is defined as being radially rigid if it has a radial strength significantly higher than self-expanding stents that is similar or greater in magnitude to that of traditional, metal balloon-expandable stents, such as those made of steel or cobalt-chromium.

When mounted serially on an inflatable balloon, they can be simultaneously implanted side-by-side in long blood vessels. During motion of the organism, the elements can move independently, maintaining their individual shape and strength while the intervening, non-stented elements of the vessel can twist, bend and rotate unencumbered. The result is a treated vessel with a rigidly maintained flow channel that still enjoys unrestricted flexibility during organismal movement.

The described embodiments exploit the principles that, (1) a rigid device that is deployed via balloon-expansion represents the optimal design of an intravascular stent given its transient effect on the arterial wall and relative ease of precise implantation, (2) a long, rigid device cannot be safely implanted in an artery that bends and twists with skeletal motion, (3) long arteries that bend and twist could be effectively treated with multiple, short BES that allow the intervening, non-stented arterial elements to move unencumbered, (4) the length, number and spacing of the stent elements could be determined by the known and predictable bending characteristics of the target arteries, and (5) arteries need only be scaffolded transiently; late dissolution of the stent will have little effect on the long-term effectiveness of treatment.

Figure 4A:
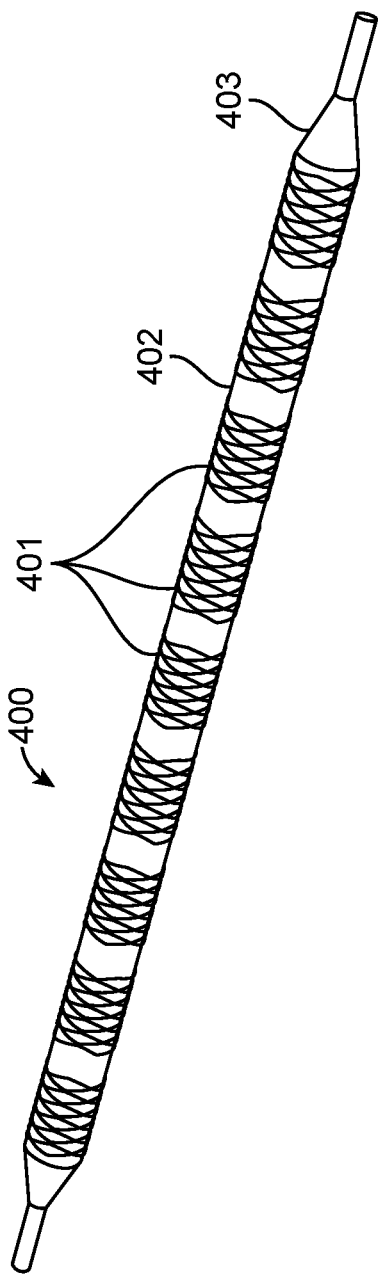
FIG. 4A illustrates one embodiment of a multi-element stent.
Figure 4B:
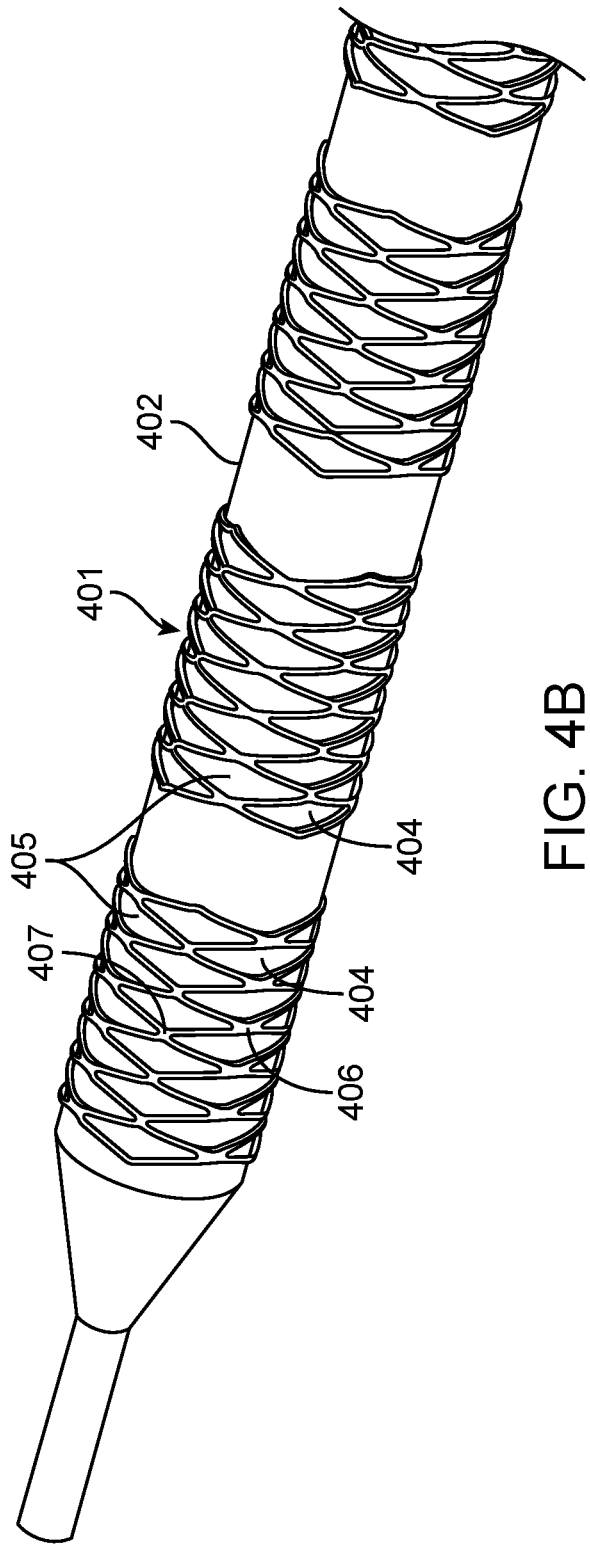
FIG. 4B is a magnified view of the stent elements in FIG. 4A.

FIG. 4A illustrates one embodiment of a multi-element stent 400, as described herein. Multi-element stent 400 comprises multiple stent elements 401. Individual balloon-expandable stent elements 401 are crimped onto an inflatable balloon 403 to facilitate delivery. FIG. 4B is a magnified view of the stent elements 401 in FIG. 4A. Individual elements 401 are positioned serially along a longitudinal length of the balloon 403 and spaced such that the stent elements 401 do not touch one another. Further, the spacing is such that after deployment, the stent elements 401 do not touch or overlap during skeletal movement. The number of elements 401, length of elements, and gap 402 between elements 401 may vary depending on the target vessel location. In an embodiment, each element 401 in the multi-element stent 400 has the same length. In multi-element stents having three or more elements 401, and thus two or more gaps 402, the gaps may be of the same length.

Figure 5A:
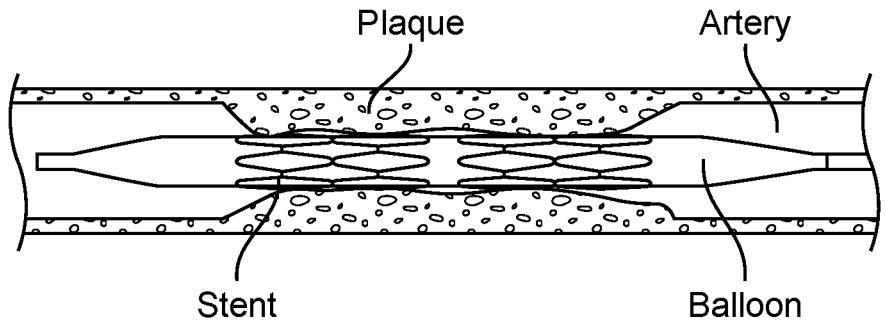
FIGS. 5A-5C depict deployment of a balloon-expandable multi-element stent.
Figure 5B:
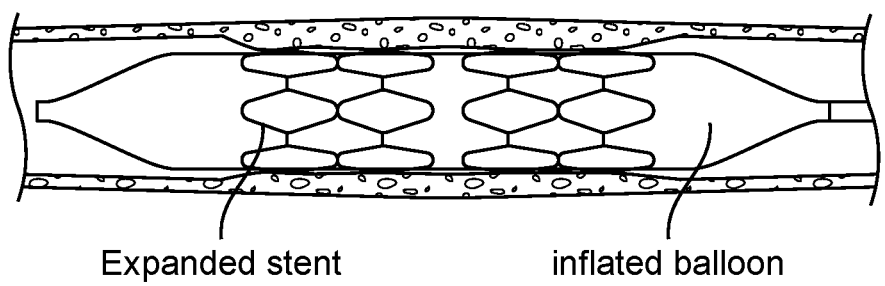
Figure 5C:
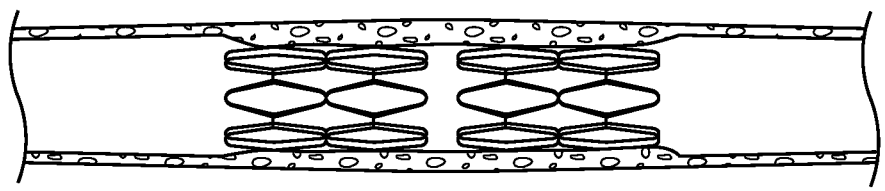

FIGS. 5A-5C depict deployment of a balloon-expandable multi-element stent. In FIG. 5A a multi-element stent mounted on a balloon is advanced to the lesion. In FIG. 5B the balloon and stent are expanded. In FIG. 5C the balloon is withdrawn leaving the multi-element stent still within the artery.

Proper stent element length and the spacing between stent elements is important given the length and persistent motion of the extremity arteries. If stent elements are too long, the stent will lack sufficient longitudinal flexibility. If the elements are placed too close together, they may overlap during movement leading to a similar lack of sufficient longitudinal flexibility. This may lead to fracture of the stent elements. Fracture of intravascular stents is clearly associated with restenosis. Likewise, if elements are too short or spaced too far apart, the lesion may not be sufficiently contact the target lesion. Proper length and spacing of the elements may be determined by the known characteristics of the target artery.

FIGS. 6A-6C are side views of a self-expanding, Nitinol stent 600 placed in a distal SFA and popliteal artery, illustrated during different amounts of leg flexion. FIG. 6A illustrates stent 600 with the leg in the neutral position, minimal flexion/mostly extended. FIG. 6B illustrates stent 600 during partial flexion (70°/20° knee/hip flexion), with a circle and bend radius 602 illustrating the angle of flexion and the curved deformation of stent 600. FIG. 6C illustrates stent 600 during greater flexion (90°/90° knee/hip flexion). As FIGS. 6A-6C illustrate, stent 600 is markedly deformed by movement of the leg. The drawn circle illustrates the use of bend radius 602 to describe the degree of deformation. Stents that bend around a small circle (with a small radius 602) are more deformed, e.g., the more deformed stent in the FIG. 6C has a smaller bend radius 602 than the less deformed stent 600 in FIG. 6B. The nearly straight stent in 6A has a very large bend radius that is too large to be accurately estimated.

Stent deformation after implantation in the femoropopliteal arteries is shown in Table 1. Perfect straightness is assigned a value of 180°. Deflection (°) is calculated as the difference between bend angles during various degrees of extremity flexion. Note the significant bending of popliteal stents as compared to SFA stents.

TABLE 1

Stent deformation after implantation in the femoropopliteal arteries.

| | SFA | SFA/prox pop | popliteal | SFA | SFA/prox pop | popliteal |
|---|---|---|---|---|---|---|
| N | 11 | 2 | 6 | 11 | 2 | 6 |
| | Measured bend angle (°) | | | Deflection (°) | | |
| neutral position | 169 ± 6 | 155 ± 11 | 167 ± 7 | | | |
| 70°/20° knee/hip flexion | 168 ± 3 | 146 ± 3 | 137 ± 18 | 4 ± 3 | 9 ± 8 | 29 ± 12* |
| 90°/90° knee/hip flexion | 165 ± 5 | 148 ± 8 | 103 ± 21 | 5 ± 2 | 8 ± 4 | 64 ± 16* |

TABLE 1-continued

Stent deformation after implantation in the femoropopliteal arteries.

| | Measured bend radius (mm) | | |
|---|---|---|---|
| 70°/20° knee/hip flexion | NA | NA | 93 ± 52 |
| 90°/90° knee/hip flexion | 135 ± 54** | NA | 22 ± 2 |

Sample sizes refer to the number of treated lesions. Data are presented as mean ± SD. NA—not applicable (stent bending deformations are minimal and bending radii are too large to be accurately measured).
*p < 0.05 as compared to SFA or SFA/prox pop.
**Stent bending radii measurable in 7 cases.

The length and spacing of the individual elements is partially determined by the planned anatomic location of the device. For instance, available anatomic and physiologic data suggest that the superficial femoral artery (SFA) is only minimally bent and compressed during flexion of the thigh and knee (bending ~7° and compression ~5%) so individual stent elements in the device intended for the SFA can therefore be fairly closely spaced; they won't overlap even when the leg is bent. In contrast, the popliteal artery more severely deforms when the hip and knee are flexed (bending ~60° and compression ~8%). Therefore, individual stent elements in the device intended for the popliteal artery must be more widely spaced so they won't overlap during skeletal movement.

Figure 7:
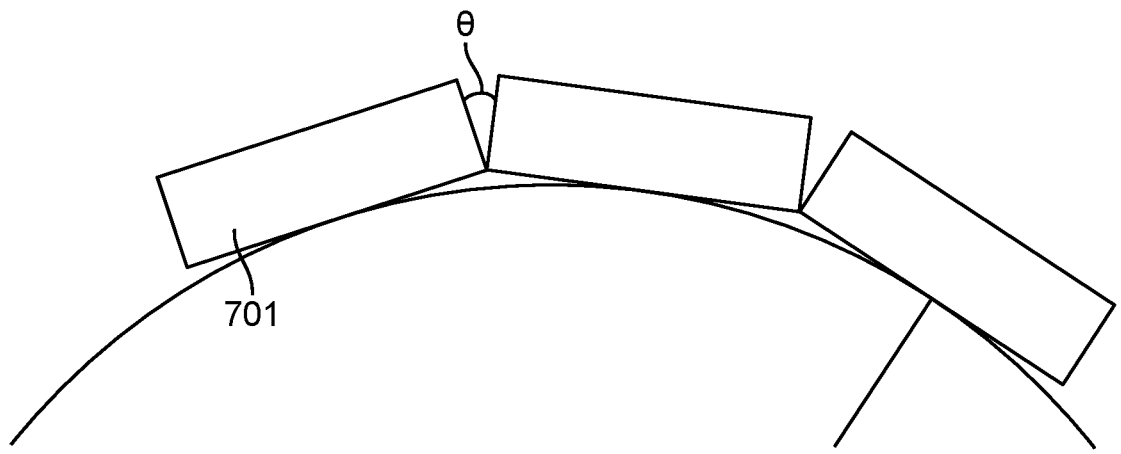
FIG. 7 depicts an angle created between stent elements during maximal flexion of the target vessel location during skeletal movement.

FIG. 7 depicts an angle θ created between stent elements 701 during maximal flexion of the target vessel location during skeletal movement. Angle θ is a calculated angle governed by the maximum bend radius and the maximum individual stent element 701 length for each anatomical location. For the SFA, angle θ is calculated to be 8.473°. For the popliteal, angle θ is calculated to be 25.609°.

In an embodiment, the minimum necessary gap between elements can be calculated using the planned stent diameter (D) in the expanded state at the target vessel location and the angle created between stent elements during maximal flexion of the vessel (θ) at the target vessel location. The gap (G) may be calculated using the formula:

$$G = \sqrt{\frac{D^2}{2}(1 - \cos\theta)}$$

As can be seen from the given formula, if all other factors remain the same, the distance between each stent element increases with an increased diameter of the stent element. Similarly, if all other factors remain the same, the distance between each stent element will be larger in the popliteal than the SFA. Table 2 shows calculated gaps using this formula.

TABLE 2

Calculated element spacing taking into account planned stent diameter and the angle created between stent elements during maximal flexion of the vessel

| Intended Anatomic Location | Maximal Deflection (°) | Maximal bend radius (mm) | Length (cm) | Diameter (mm) | Element Length (mm) | Number of Elements | Element Spacing (mm) |
|---|---|---|---|---|---|---|---|
| SFA | 8 | 135 | 30 | 5.0 | 15 | 2 | 0.37 |
| SFA | 8 | 135 | 30 | 6.0 | 15 | 2 | 0.44 |
| SFA | 8 | 135 | 40 | 5.0 | 20 | 2 | 0.37 |
| SFA | 8 | 135 | 40 | 6.0 | 20 | 2 | 0.44 |
| SFA | 8 | 135 | 60 | 5.0 | 20 | 3 | 0.37 |
| SFA | 8 | 135 | 60 | 6.0 | 20 | 3 | 0.44 |
| SFA | 8 | 135 | 80 | 5.0 | 20 | 4 | 0.37 |
| SFA | 8 | 135 | 80 | 6.0 | 20 | 4 | 0.44 |
| SFA | 8 | 135 | 80 | 8.0 | 20 | 4 | 0.59 |
| SFA | 8 | 135 | 100 | 3.0 | 20 | 5 | 0.22 |
| SFA | 8 | 135 | 100 | 4.0 | 20 | 5 | 0.30 |
| SFA | 8 | 135 | 100 | 5.0 | 20 | 5 | 0.37 |
| SFA | 8 | 135 | 100 | 6.0 | 20 | 5 | 0.44 |
| SFA | 8 | 135 | 100 | 8.0 | 20 | 5 | 0.59 |
| Popliteal | 64 | 22 | 20 | 4.0 | 10 | 2 | 0.89 |
| Popliteal | 64 | 22 | 20 | 5.0 | 10 | 2 | 1.11 |
| Popliteal | 64 | 22 | 30 | 4.0 | 10 | 3 | 0.89 |
| Popliteal | 64 | 22 | 30 | 5.0 | 10 | 3 | 1.11 |
| Popliteal | 64 | 22 | 40 | 4.0 | 10 | 4 | 0.89 |
| Popliteal | 64 | 22 | 40 | 5.0 | 10 | 4 | 1.11 |
| Popliteal | 64 | 22 | 60 | 4.0 | 10 | 6 | 0.89 |
| Popliteal | 64 | 22 | 60 | 5.0 | 10 | 6 | 1.11 |
| Popliteal | 64 | 22 | 80 | 4.0 | 10 | 8 | 0.89 |
| Popliteal | 64 | 22 | 80 | 5.0 | 10 | 8 | 1.11 |
| Popliteal | 64 | 22 | 100 | 3.0 | 10 | 10 | 0.66 |
| Popliteal | 64 | 22 | 100 | 4.0 | 10 | 10 | 0.89 |
| Popliteal | 64 | 22 | 100 | 5.0 | 10 | 10 | 1.11 |

TABLE 2-continued

Calculated element spacing taking into account planned stent diameter and the angle created between stent elements during maximal flexion of the vessel

| Intended Anatomic Location | Maximal Deflection (°) | Maximal bend radius (mm) | Length (cm) | Diameter (mm) | Element Length (mm) | Number of Elements | Element Spacing (mm) |
|---|---|---|---|---|---|---|---|
| Popliteal | 64 | 22 | 100 | 6.0 | 10 | 10 | 1.33 |
| Popliteal | 64 | 22 | 100 | 8.0 | 10 | 10 | 1.77 |

Ideal gap length between stent elements may also be influenced by axial stent compression or shortening during extremity flexion. Table 3 shows axial stent compression after implantation in the femoropopliteal arteries. The amount of axial compression is calculated as the difference between measured stent lengths during various degrees of extremity flexion.

As can be seen from this formula, if all other factors remain the same, the distance between each stent element increases with an increase in length of the stent elements. Likewise, if all other factors remain the same, the distance between each stent element decreases with an increase in the number of elements in the multi-element stent. Similarly, if all other factors remain the same, the distance between each

TABLE 3

Axial stent compression after implantation in the femoropopliteal arteries

| | Measured stent length (mm) | | | Axial compression (%) | | |
|---|---|---|---|---|---|---|
| | SFA | SFA/prox pop | popliteal | SFA | SFA/prox pop | popliteal |
| Single 80 mm stents | | | | | | |
| N | 6 | 1 | 1 | 6 | 1 | 1 |
| neutral position | 80 ± 2 | 73 | 79 | | | |
| 70°/20° knee/hip flexion | 78 ± 2 | 72 | 76 | 2.0 ± 1.8 | 2.7 | 3.1 |
| 90°/90° knee/hip flexion | 77 ± 2 | 70 | 71 | 3.5 ± 2.1 | 5.0 | 9.3 |
| Single 100 mm stents | | | | | | |
| N | 4 | 1 | 3 | 4 | 1 | 3 |
| neutral position | 101 ± 2 | 94 | 100 ± 3 | | | |
| 70°/20° knee/hip flexion | 99 ± 3 | 92 | 98 ± 1 | 1.4 ± 1.9 | 2.1 | 2.0 ± 1.7 |
| 90°/90° knee/hip flexion | 98 ± 1 | 88 | 92 ± 6 | 2.9 ± 1.4 | 5.7 | 8.4 ± 5.0 |
| Overlapped stents | | | | | | |
| N | 1 | | 2 | 1 | | 2 |
| neutral position | 96.6 | | 118 ± 75 | | | |
| 70°/20° knee/hip flexion | 96.5 | | 112 ± 74 | 0.1 | | 6.1 ± 3.0 |
| 90°/90° knee/hip flexion | 89.8 | | 108 ± 70 | 7.0 | | 8.4 ± 1.6 |
| All stents (including overlapped) | | | | | | |
| N | 11 | 2 | 6 | 11 | 2 | 6 |
| neutral position | 91 ± 14 | 84 ± 14 | 102 ± 36 | | | |
| 70°/20° knee/hip flexion | 90 ± 15 | 82 ± 14 | 99 ± 35 | 1.7 ± 1.7 | 2.4 ± 0.4 | 3.5 ± 2.7 |
| 90°/90° knee/hip flexion | 88 ± 15 | 79 ± 13 | 94 ± 35 | 3.1 ± 1.8 | 5.3 ± 0.5 | 8.5 ± 3.2* |

Sample sizes refer to the number of treated lesions. Data are presented as mean ± SD.
*p < 0.05 as compared to SFA.

Ideal gap length taking into account axial compression may be calculated using the formula:

$$Gap = ((LEC + GEC - GC)/(e-1)) + G$$

L is the stent element length. E is the number of stent elements. G is the gap length calculated using the previous formula. C is the maximum percent axial compression for the target vessel location. For the SFA, C is approximately 5%. For the popliteal, C is approximately 8%.

stent element increases with an increase of the maximum percent axial compression of the stent elements at the target vessel location. The approximate relationship between device diameter, length, number of elements and element spacing for devices intended for the superficial femoral artery are shown in Table 4. The approximate relationship between device diameter, length, number of elements and element spacing for devices intended for the popliteal artery are shown in Table 5.

TABLE 4

The approximate relationship between device diameter, length, number of elements and element spacing for devices intended for the superficial femoral artery

| Maximal Deflection (°) | Maximal bend radius (mm) | Maximal axial compression (%) | Length (mm) | Diameter (mm) | Element Length (mm) | Number of Elements | Element Spacing (mm) |
|---|---|---|---|---|---|---|---|
| 8 | 135 | 5 | 20 | 3.0 | 10 | 2 | 1.23 |
| 8 | 135 | 5 | 20 | 4.0 | 10 | 2 | 1.31 |
| 8 | 135 | 5 | 20 | 5.0 | 10 | 2 | 1.39 |
| 8 | 135 | 5 | 20 | 6.0 | 10 | 2 | 1.47 |
| 8 | 135 | 5 | 20 | 8.0 | 10 | 2 | 1.62 |
| 8 | 135 | 5 | 30 | 3.0 | 15 | 2 | 1.73 |
| 8 | 135 | 5 | 30 | 4.0 | 15 | 2 | 1.81 |
| 8 | 135 | 5 | 30 | 5.0 | 15 | 2 | 1.89 |
| 8 | 135 | 5 | 30 | 6.0 | 15 | 2 | 1.97 |
| 8 | 135 | 5 | 30 | 8.0 | 15 | 2 | 2.12 |
| 8 | 135 | 5 | 40 | 3.0 | 20 | 2 | 2.23 |
| 8 | 135 | 5 | 40 | 4.0 | 20 | 2 | 2.31 |
| 8 | 135 | 5 | 40 | 5.0 | 20 | 2 | 2.39 |
| 8 | 135 | 5 | 40 | 6.0 | 20 | 2 | 2.47 |
| 8 | 135 | 5 | 40 | 8.0 | 20 | 2 | 2.62 |
| 8 | 135 | 5 | 60 | 3.0 | 20 | 3 | 1.73 |
| 8 | 135 | 5 | 60 | 4.0 | 20 | 3 | 1.81 |
| 8 | 135 | 5 | 60 | 5.0 | 20 | 3 | 1.89 |
| 8 | 135 | 5 | 60 | 6.0 | 20 | 3 | 1.97 |
| 8 | 135 | 5 | 60 | 8.0 | 20 | 3 | 2.12 |
| 8 | 135 | 5 | 80 | 3.0 | 20 | 4 | 1.57 |
| 8 | 135 | 5 | 80 | 4.0 | 20 | 4 | 1.64 |
| 8 | 135 | 5 | 80 | 5.0 | 20 | 4 | 1.72 |
| 8 | 135 | 5 | 80 | 6.0 | 20 | 4 | 1.80 |
| 8 | 135 | 5 | 80 | 8.0 | 20 | 4 | 1.95 |
| 8 | 135 | 5 | 100 | 3.0 | 20 | 5 | 1.48 |
| 8 | 135 | 5 | 100 | 4.0 | 20 | 5 | 1.56 |
| 8 | 135 | 5 | 100 | 5.0 | 20 | 5 | 1.64 |
| 8 | 135 | 5 | 100 | 6.0 | 20 | 5 | 1.72 |
| 8 | 135 | 5 | 100 | 8.0 | 20 | 5 | 1.87 |

TABLE 5

The approximate relationship between device diameter, length, number of elements and element spacing for devices intended for the popliteal artery

| Maximal Deflection (°) | Maximal bend radius (mm) | Maximal axial compression (%) | Length (mm) | Diameter (mm) | Element Length (mm) | Number of Elements | Element Spacing (mm) |
|---|---|---|---|---|---|---|---|
| 64 | 22 | 8 | 20 | 3.0 | 10 | 2 | 2.32 |
| 64 | 22 | 8 | 20 | 4.0 | 10 | 2 | 2.56 |
| 64 | 22 | 8 | 20 | 5.0 | 10 | 2 | 2.80 |
| 64 | 22 | 8 | 20 | 6.0 | 10 | 2 | 3.04 |
| 64 | 22 | 8 | 20 | 8.0 | 10 | 2 | 3.51 |
| 64 | 22 | 8 | 30 | 3.0 | 10 | 3 | 1.92 |
| 64 | 22 | 8 | 30 | 4.0 | 10 | 3 | 2.16 |
| 64 | 22 | 8 | 30 | 5.0 | 10 | 3 | 2.40 |
| 64 | 22 | 8 | 30 | 6.0 | 10 | 3 | 2.64 |
| 64 | 22 | 8 | 30 | 8.0 | 10 | 3 | 3.11 |
| 64 | 22 | 8 | 40 | 3.0 | 10 | 4 | 1.78 |
| 64 | 22 | 8 | 40 | 4.0 | 10 | 4 | 2.02 |
| 64 | 22 | 8 | 40 | 5.0 | 10 | 4 | 2.26 |
| 64 | 22 | 8 | 40 | 6.0 | 10 | 4 | 2.50 |
| 64 | 22 | 8 | 40 | 8.0 | 10 | 4 | 2.98 |
| 64 | 22 | 8 | 60 | 3.0 | 10 | 6 | 1.68 |
| 64 | 22 | 8 | 60 | 4.0 | 10 | 6 | 1.92 |
| 64 | 22 | 8 | 60 | 5.0 | 10 | 6 | 2.16 |
| 64 | 22 | 8 | 60 | 6.0 | 10 | 6 | 2.40 |
| 64 | 22 | 8 | 60 | 8.0 | 10 | 6 | 2.87 |
| 64 | 22 | 8 | 80 | 3.0 | 10 | 8 | 1.63 |
| 64 | 22 | 8 | 80 | 4.0 | 10 | 8 | 1.87 |
| 64 | 22 | 8 | 80 | 5.0 | 10 | 8 | 2.11 |
| 64 | 22 | 8 | 80 | 6.0 | 10 | 8 | 2.35 |
| 64 | 22 | 8 | 80 | 8.0 | 10 | 8 | 2.83 |
| 64 | 22 | 8 | 100 | 3.0 | 10 | 10 | 1.61 |
| 64 | 22 | 8 | 100 | 4.0 | 10 | 10 | 1.85 |

TABLE 5-continued

The approximate relationship between device diameter, length, number of elements and element spacing for devices intended for the popliteal artery

| Maximal Deflection (°) | Maximal bend radius (mm) | Maximal axial compression (%) | Length (mm) | Diameter (mm) | Element Length (mm) | Number of Elements | Element Spacing (mm) |
|---|---|---|---|---|---|---|---|
| 64 | 22 | 8 | 100 | 5.0 | 10 | 10 | 2.09 |
| 64 | 22 | 8 | 100 | 6.0 | 10 | 10 | 2.33 |
| 64 | 22 | 8 | 100 | 8.0 | 10 | 10 | 2.80 |

Figure 8A:
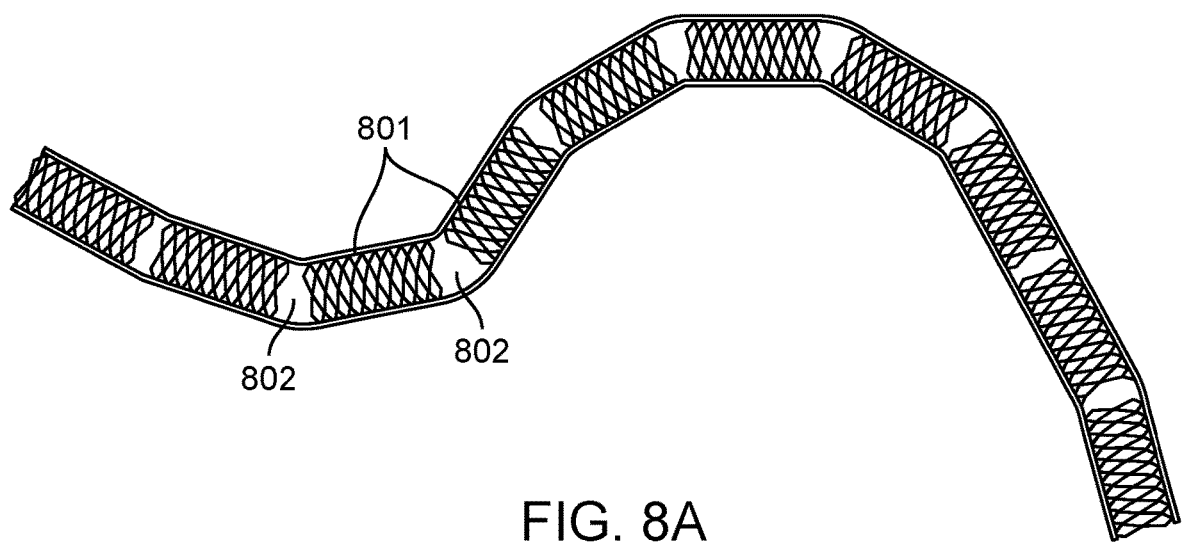
FIG. 8A shows an implanted multi-element stent in a popliteal artery during full flexion of the hip and knee.
Figure 8B:
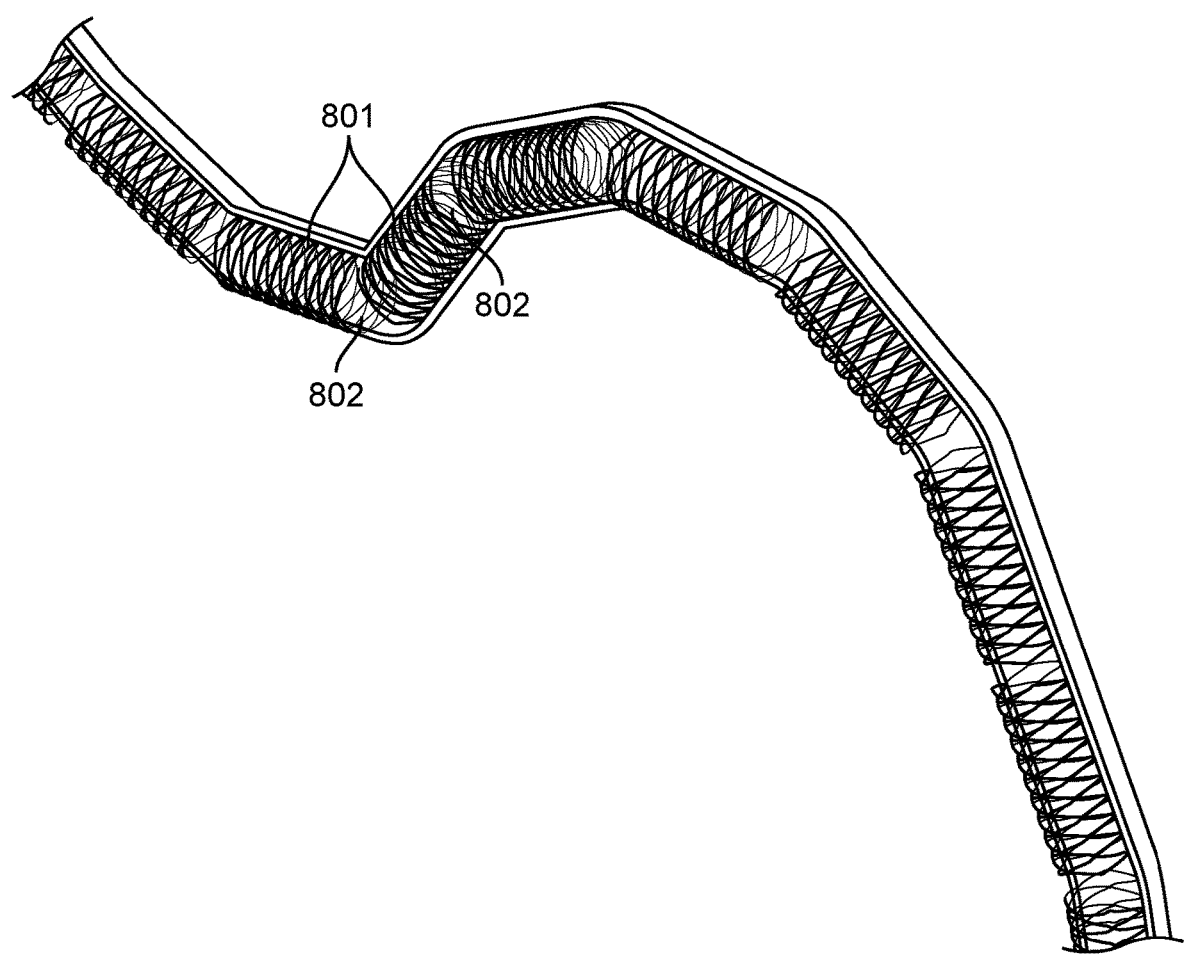
FIG. 8B depicts the implanted device of FIG. 8A shown in three dimensions.

FIG. 8A shows an implanted multi-element stent in a popliteal artery during full flexion of the hip and knee. FIG. 8B depicts the implanted device of FIG. 8A shown in three dimensions. The individual stent elements 801 are spaced such that they do not overlap even when the artery is highly bent. Unencumbered arterial movement is afforded through flexion or extension of the unstented gaps 802.

The stents described herein may be formed from various different materials. In an embodiment, stents may be formed from materials comprising metals such as magnesium, stainless steel, platinum chromium, or cobalt chromium, or the like.

Alternatively, stents may be formed from a polymer. In an embodiment, stents or stent elements may be fabricated using non-bioresorbable material, including 1,6-hexanediol diacrylate with 2% DMPA as a photoinitiator, and 0.10% Tinuvin 327 as a light absorber. In various alternative embodiments, the stent or stent element may be made from any suitable bioresorbable material, such as but not limited to poly(L-lactic acid) (PLLA), polyglycolic acid (PGA), poly(iodinated desaminotyrosyl-tyrosine ethyl ester) carbonate, or the like.

In alternative embodiments, any suitable polymer may be used to construct the stent. The term "polymer" is intended to include a product of a polymerization reaction inclusive of homopolymers, copolymers, terpolymers, etc., whether natural or synthetic, including random, alternating, block, graft, branched, cross-linked, blends, compositions of blends and variations thereof. The polymer may be in true solution, saturated, or suspended as particles or supersaturated in the beneficial agent. The polymer can be biocompatible, or biodegradable. For purpose of illustration and not limitation, the polymeric material may include, but is not limited to, poly(D-lactic acid) (PDLA), poly(D,L-lactic acid) (PDLLA), poly(iodinated desamino tyrosyl-tyrosine ethyl ester) carbonate, poly(lactic-co-glycolic acid) (PLGA), salicylate based polymer, semicrystalline polylactide, phosphorylcholine, polycaprolactone (PCL), poly-D,L-lactic acid, poly-L-lactic acid, poly(lactideco-glycolide), poly(hydroxybutyrate), poly(hydroxybutyrate-co-valerate), polydioxanone (PDS), polyorthoester, polyanhydride, poly(glycolic acid), poly(glycolic acid-co-trimethylene carbonate), polyphosphoester, polyphosphoester urethane, poly(amino acids), cyanoacrylates, poly(trimethylene carbonate), poly (iminocarbonate), polyalkylene oxalates, polyphosphazenes, polyiminocarbonates, and aliphatic polycarbonates, fibrin, fibrinogen, cellulose, starch, collagen, polyurethane including polycarbonate urethanes, polyethylene, polyethylene terephthalate, ethylene vinyl acetate, ethylene vinyl alcohol, silicone including polysiloxanes and substituted polysiloxanes, polyethylene oxide, polybutylene terephthalate-co-PEG, PCL-co-PEG, PLA-co-PEG, PLLA-co-PCL, polyacrylates, polyvinyl pyrrolidone, polyacrylamide, and combinations thereof. Non-limiting examples of other suitable polymers include thermoplastic elastomers in general, polyolefin elastomers, EPDM rubbers and polyamide elastomers, and biostable plastic material including acrylic polymers, and its derivatives, nylon, polyesters and expoxies. In some embodiments, the stent may include one or more coatings, with materials like poly(D,L-lactic acid) (PDLLA). These materials are merely examples, however, and should not be seen as limiting the scope of the invention.

Stent elements may comprise various shapes and configurations. Some or all of the stent elements may comprise closed-cell structures formed by intersecting struts. Closed-cell structures may comprise diamond, square, rectangular, parallelogrammatic, triangular, pentagonal, hexagonal, heptagonal, octagonal, clover, lobular, circular, elliptical, and/or ovoid geometries. Closed-cells may also comprise slotted shapes such as H-shaped slots, I-shaped slots, J-shaped slots, and the like. Additionally or alternatively, stent may comprise open cell structures such as spiral structures, serpentine structures, zigzags structures, etc. Strut intersections may form pointed, perpendicular, rounded, bullnosed, flat, beveled, and/or chamfered cell corners. In an embodiment, stent may comprise multiple different cells having different cell shapes, orientations, and/or sizes. Various cell structures have been described in PCT International Application Number PCT/US16/20743, entitled "MULTI-ELEMENT BIORESORBABLE INTRAVASCULAR STENT", the full disclosure of which is herein incorporated by reference. In an embodiment, stent elements may comprise a plurality of diamond shaped closed cells longer in a longitudinal direction than in a radial direction when in an unexpanded state. The stent elements may also comprise a plurality of diamond shaped closed cells longer in a radial direction than in a longitudinal direction in the expanded state.

Returning to FIG. 4B, in this exemplary embodiment, the stent elements 401 have a diamond shaped closed-cell pattern. Elements 401 comprise intermixed diamond shaped closed cells 404, 405. Diamond shaped cells 404 may be aligned in the longitudinal and/or the circumferential directions in a repeating pattern. Similarly, diamond shaped cells 405 may be aligned in the longitudinal and/or the circumferential directions in a repeating pattern. Additionally or alternatively, diamond shaped cells 404 and diamond shaped cells 405 may be helically aligned in an alternating pattern. In an embodiment, diamond shaped cells 404 and diamond shaped cells 405 are circumferentially offset. Additionally, diamond shaped cells 405 may be formed at a central location between four adjacent diamond shaped cells 404. The width of struts 406 between two corners of longitudinally aligned diamond shaped cells 404 are larger than the width of struts 407 between two corners of longitudinally aligned diamond shaped cells 405.

Figure 9A:
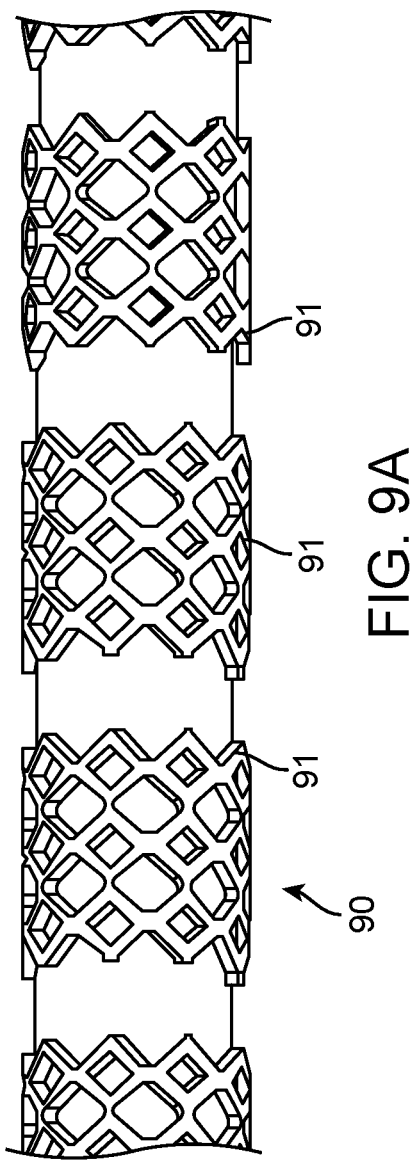
FIG. 9A illustrates an alternative embodiment of a multi-element stent.
Figure 9B:
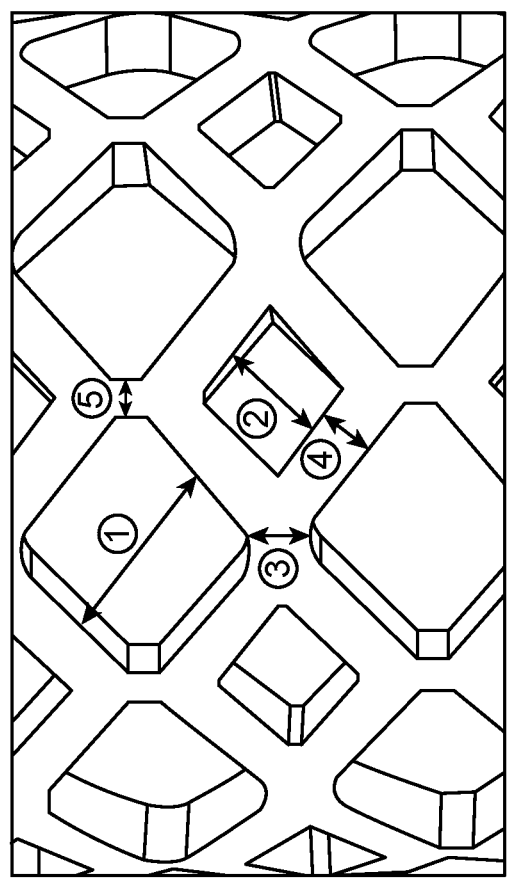
FIG. 9B is a magnified view of the stent elements in FIG. 9A.

FIG. 9A illustrates an alternative embodiment of a multi-element stent. FIG. 9B is a magnified view of the stent elements in FIG. 9A. The stent may have a diamond or other closed-cell pattern. In this embodiment, the stent comprises intermixed large and small cells. Large cells may be aligned in the longitudinal and/or the circumferential directions in a repeating pattern. Similarly, small cells may be aligned in the longitudinal and/or the circumferential directions in a repeating pattern. Additionally or alternatively, small and large cells may be helically aligned in an alternating pattern. In an embodiment, small cells and large cells are circumferentially offset. Additionally, small cells may be formed at a central location between four adjacent large cells. In an embodiment illustrated in FIG. 9B, a first opening dimension (1) of a large closed cell is about 0.68 mm, a second opening dimension (2) of an adjacent small closed cell is about 0.39 mm, a third dimension (3) of a width of a strut between two up-to-down corners of the longitudinally aligned large closed cells is about 0.25 mm, a fourth dimension (4) of a width of a strut between two straight portions of the helically aligned large closed cell and small closed cell is about 0.2 mm, and a fifth dimension (5) of a width of a strut between two side-to-side corners of the circumferentially aligned large closed cells is about 0.12 mm. These measurements are provided for exemplary purposes only and are not intended to limit the scope of the invention.

In some embodiments, at least one wider strut extends between multiple cells to form a spiral along a length of the stent elements to enhance the radial strength of each of the stent elements. In some embodiments, the wider strut extends from one end to an opposite end of one of the stent elements. In other embodiments, the wider strut does not extend from one end to an opposite end of one of the stent elements.

Figure 10A:
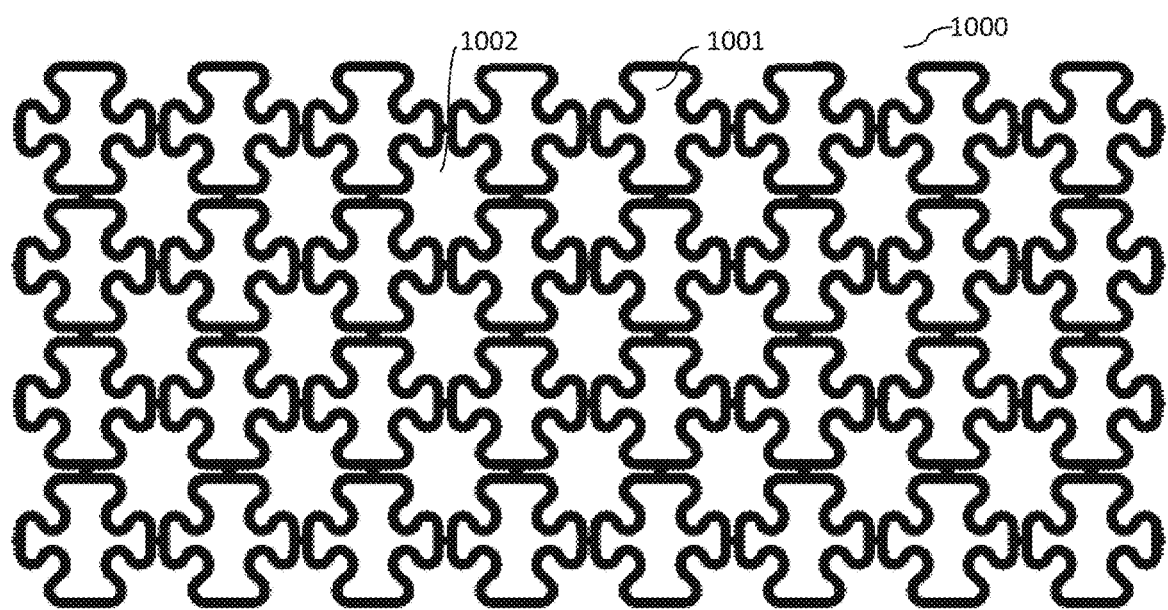
FIG. 10A is a two-dimensional depiction of an element having a lobular cell structure.
Figure 10B:
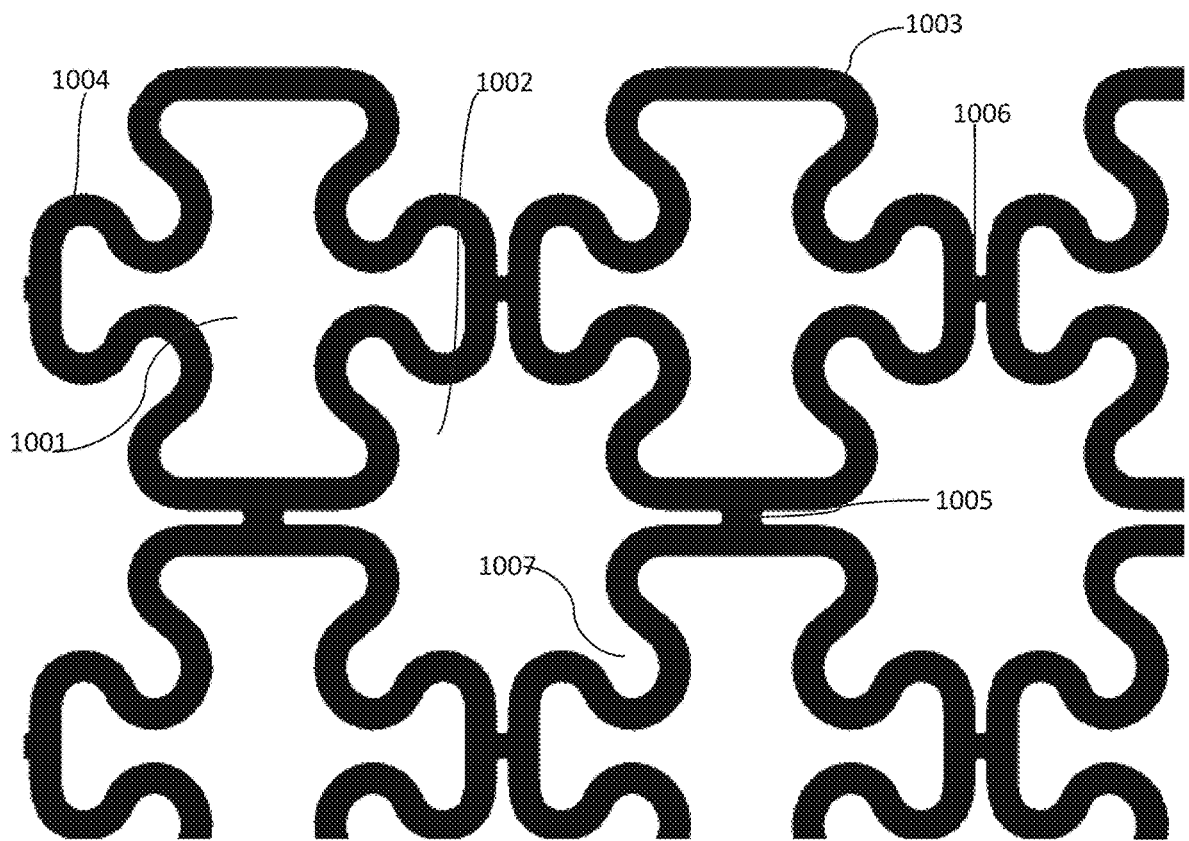
FIG. 10B is a magnified view of the cells in FIG. 10A.
Figure 10C:
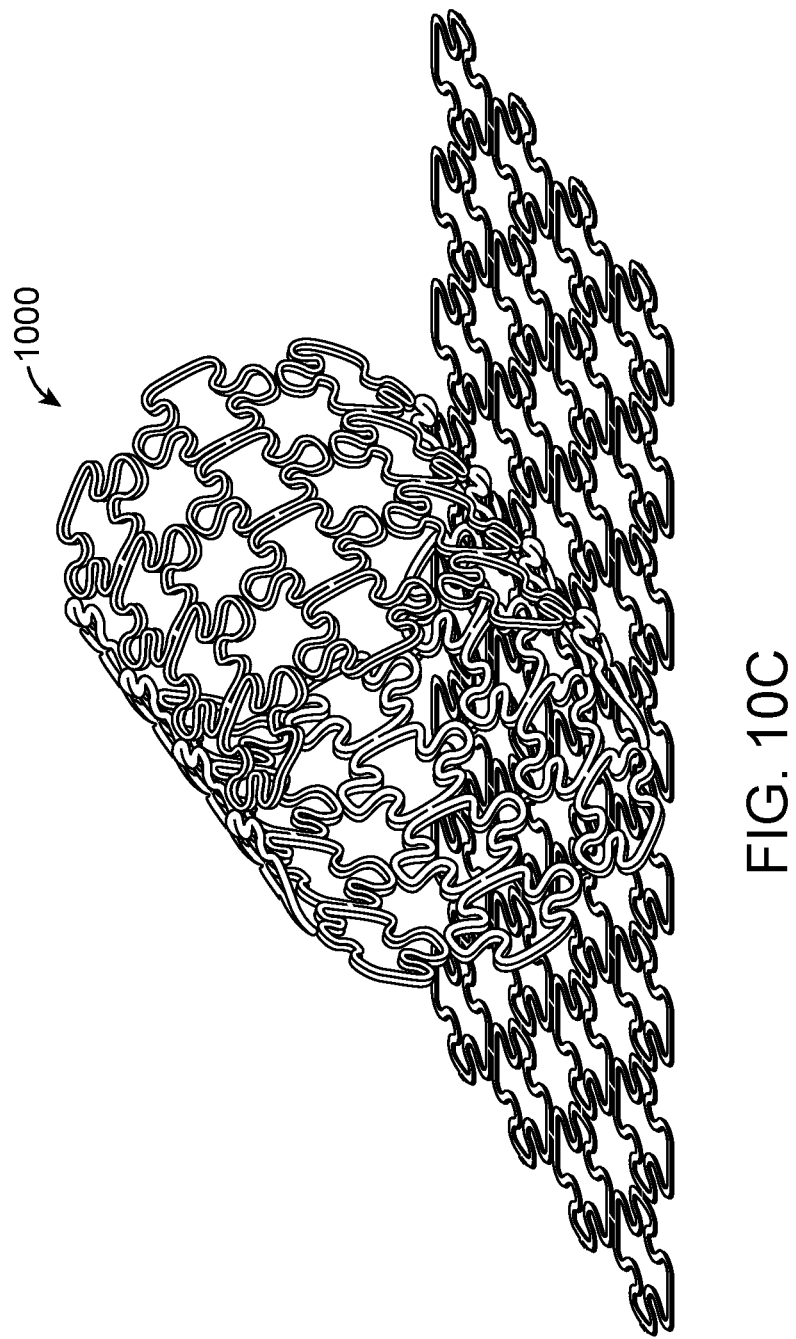
FIG. 10C shows the stent element of FIG. 10A in cylindrical form.

FIGS. 10A-10C illustrate an embodiment of a stent element having a clover or lobular cell configuration. While FIGS. 10A-10C depict cells with four lobes, cells may have any number of lobes. FIG. 10A is a two-dimensional depiction of an element having a lobular cell structure. FIG. 10B is a magnified view of the cells in FIG. 10A. FIG. 10C shows the stent element of FIG. 10A in cylindrical form wherein the two dimensional cells of FIG. 10A are wrapped from left to right to form a cylinder. In this embodiment, element 1000 comprises intermixed lobular closed cells 1001, 1002. Lobular cells 1001 may be aligned in the longitudinal and/or the circumferential directions in a repeating pattern. Similarly, lobular cells 1002 may be aligned in the longitudinal and/or the circumferential directions in a repeating pattern. Additionally or alternatively, lobular cells 1002 and lobular cells 1001 may be helically aligned in an alternating pattern. In an embodiment, lobular cells 1002 and lobular cells 1001 are circumferentially offset. Additionally, lobular cells 1002 may be formed at a central location between four adjacent lobular cells 1001. In an embodiment illustrated in FIGS. 10A-10C, longitudinal lobes 1003 aligned longitudinally are larger than circumferential lobes 1004 aligned circumferentially. Alternatively, longitudinal lobes 1003 may be the same size as circumferential lobes 1004. Longitudinal lobes 1003 of adjacent longitudinally aligned lobular cells 1001 may be connected by longitudinal connecting struts 1005. Circumferential lobes 1004 of adjacent circumferentially aligned lobular cells 1001 may be connected by circumferential connecting struts 1006. In an embodiment, longitudinal connecting struts 1005 are wider than circumferential connecting struts 1006. Alternatively, longitudinal connecting struts 1005 may have the same widths as circumferential connecting struts 1006. Element 1000 may take a crimped form when mounted on an unexpanded balloon. Likewise, element 1000 may take an expanded form when expanded by a balloon. Concavities 1007 move away from the center of lobular element 1000 as the lobular cell 1001 moves from a crimped state to an expanded state.

Figure 11A:
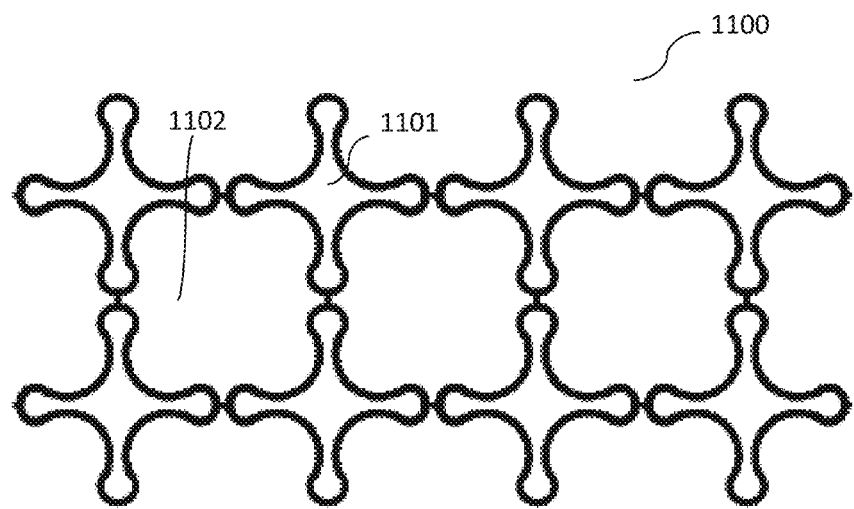
FIG. 11A is a two-dimensional depiction of an element having an alternative lobular cell structure.
Figure 11B:
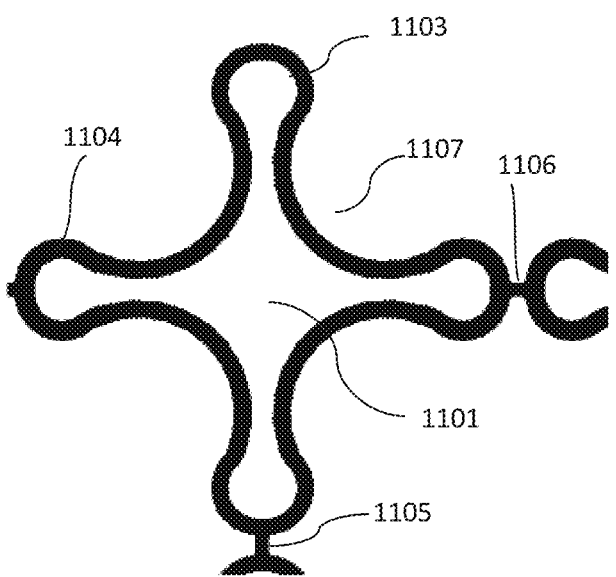
FIG. 11B is a magnified view of a cell in FIG. 11A.

FIGS. 11A-11B illustrate an alternative embodiment of a stent element having a clover or lobular cell configuration. While FIGS. 11A-11B depict cells with four lobes, cells may have any number of lobes. FIG. 11A is a two-dimensional depiction of an element having this lobular cell structure. FIG. 11B is a magnified view of a cell in FIG. 11A. A stent element with the cell structure of FIG. 11A would have a wrap orientation of left to right to form a cylinder. In this embodiment, element 1100 comprises intermixed lobular closed cells 1101, 1102. Lobular cells 1101 may be aligned in the longitudinal and/or the circumferential directions in a repeating pattern. Similarly, lobular cells 1102 may be aligned in the longitudinal and/or the circumferential directions in a repeating pattern. Additionally or alternatively, lobular cells 1102 and lobular cells 1101 may be helically aligned in an alternating pattern. In an embodiment, lobular cells 1102 and lobular cells 1101 are circumferentially offset. Additionally, lobular cells 1102 may be formed at a central location between four adjacent lobular cells 1101. In an embodiment, longitudinal lobes 1103 aligned longitudinally may be larger than circumferential lobes 1104 aligned circumferentially. Alternatively, longitudinal lobes 1103 may be the same size as circumferential lobes 1104. Longitudinal lobes 1103 of adjacent longitudinally aligned lobular cells 1101 may be connected by longitudinal connecting struts 1105. Circumferential lobes 1104 of adjacent circumferentially aligned lobular cells 1101 may be connected by circumferential connecting struts 1106. In an embodiment, longitudinal connecting struts 1105 are wider than circumferential connecting struts 1106. Alternatively, longitudinal connecting struts 1105 may have the same widths as circumferential connecting struts 1106. Element 1100 may take a crimped form when mounted on an unexpanded balloon. Likewise, element 1100 may take an expanded form when expanded by a balloon. Concavities 1107 move away from the center of lobular cell 1101 as the lobular element 1100 moves from a crimped state to an expanded state.

Figure 12A:
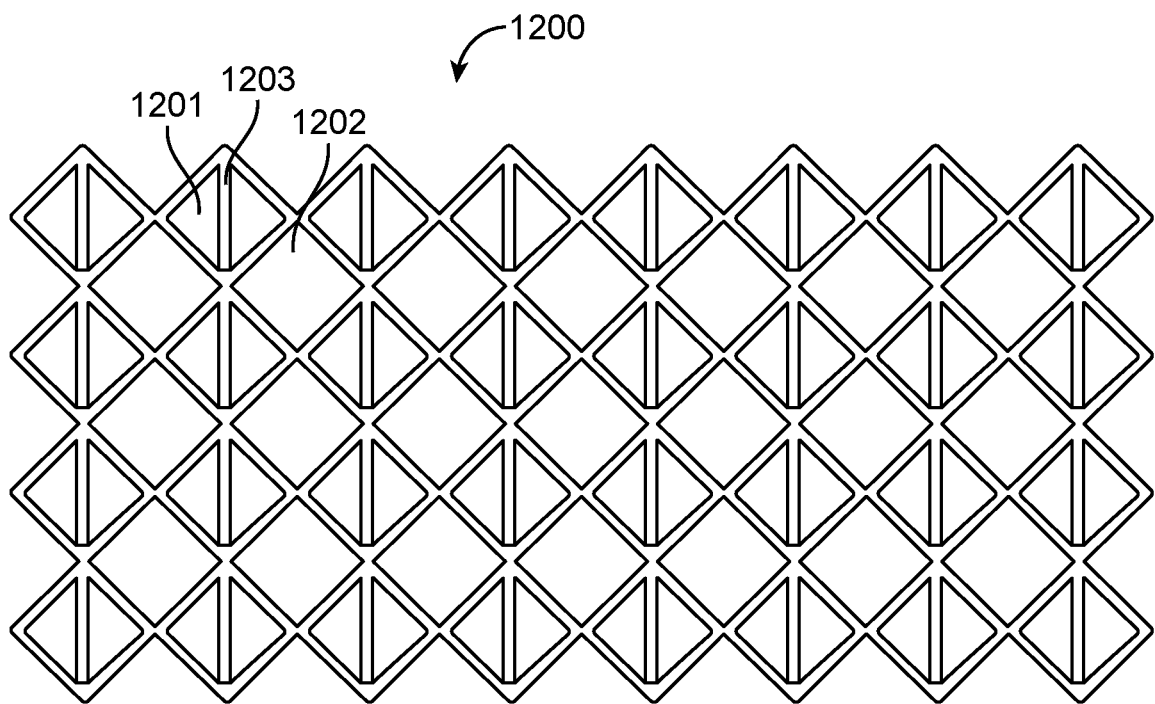
FIG. 12A is a two-dimensional depiction of an element having a ratcheting configuration.
Figure 12B:
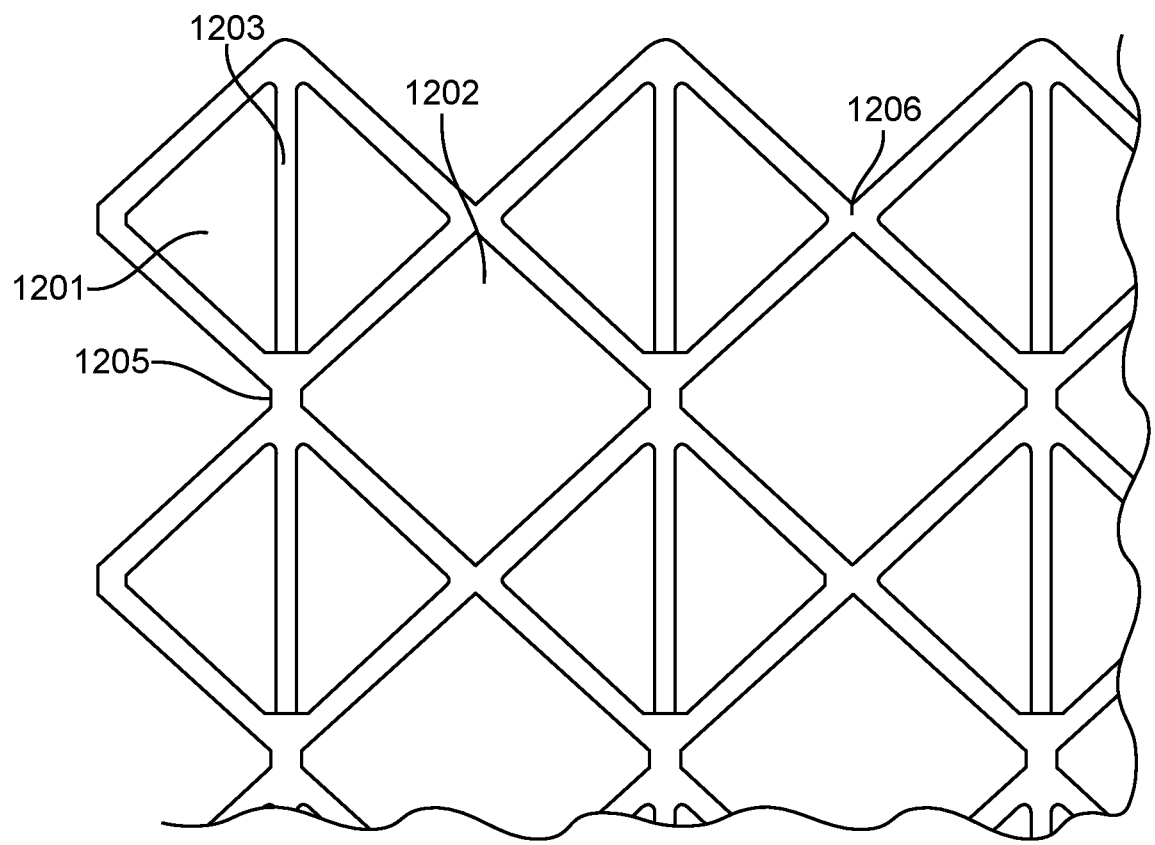
FIG. 12B is a magnified view of the cells in FIG. 12A.
Figure 12C:
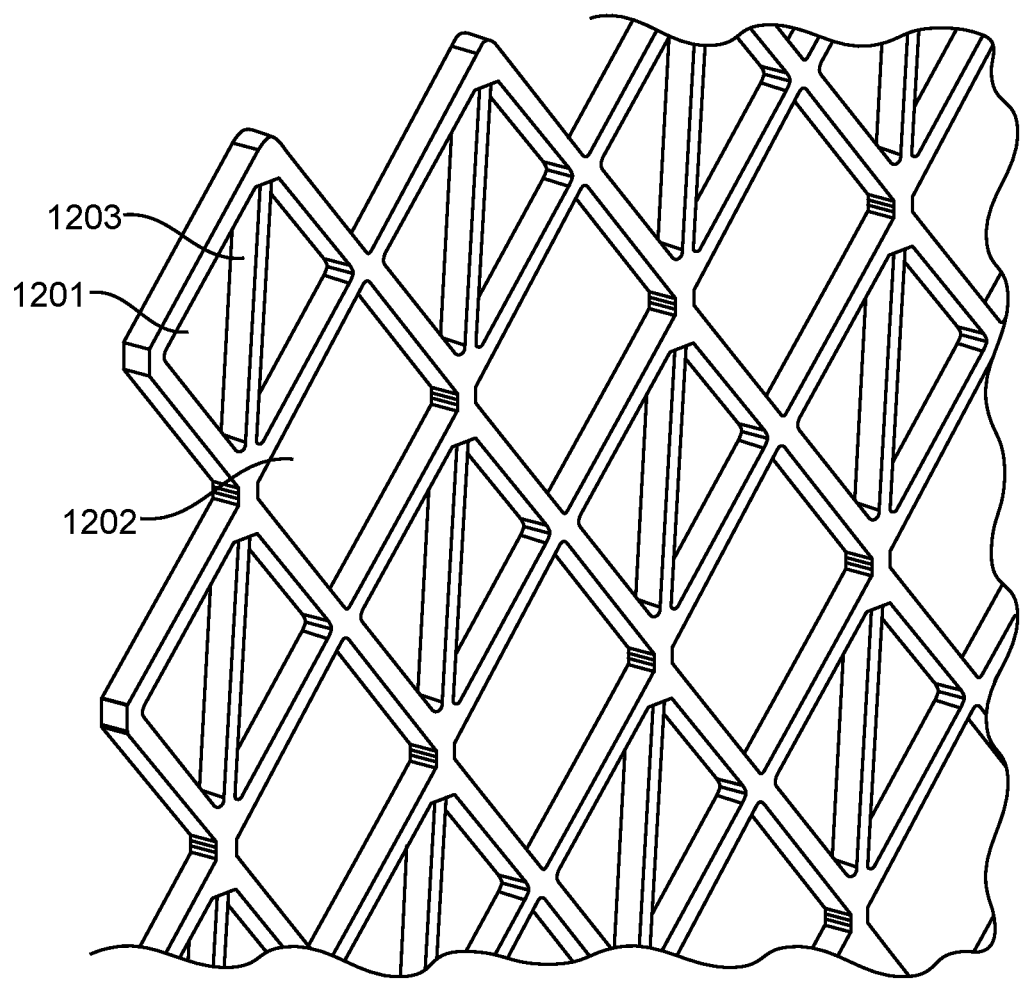
FIG. 12C is an isometric view of the cells in FIG. 12A.
Figure 12D:
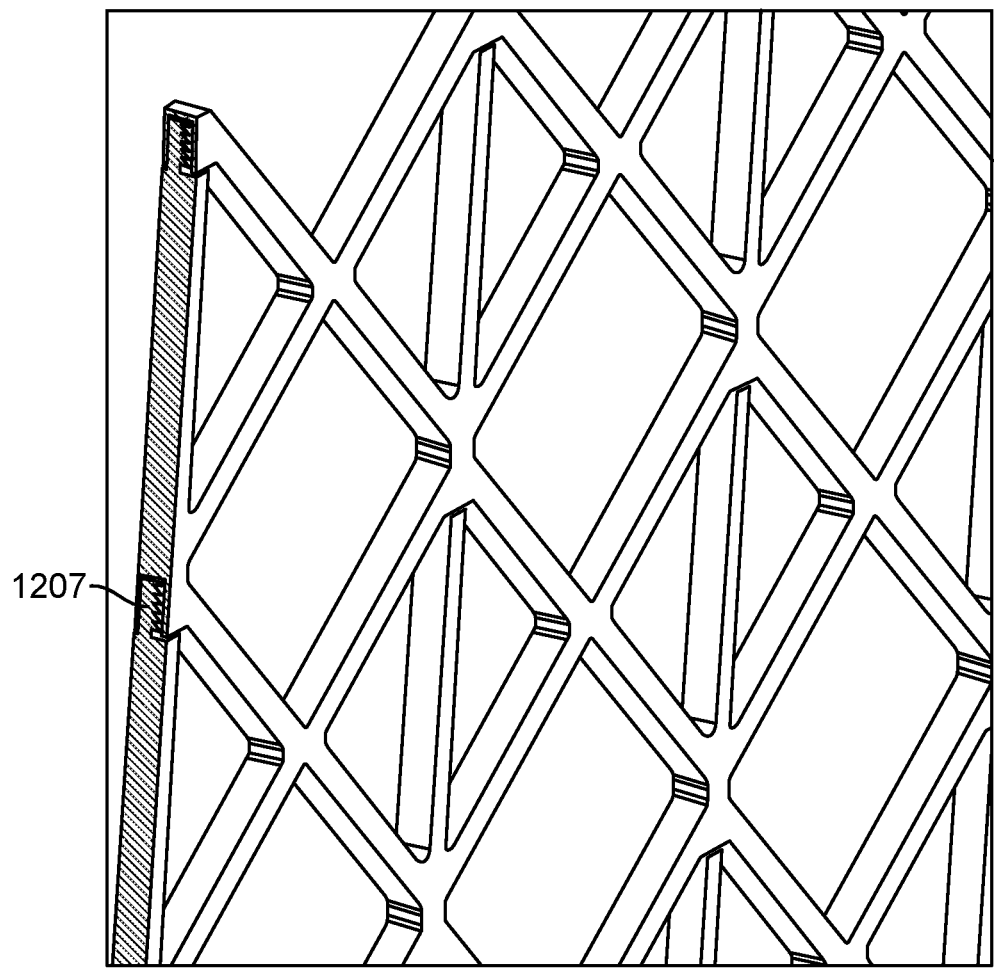
FIG. 12D is a cross-sectional view of the cells in FIG. 12C showing a ratchet.
Figure 12E:
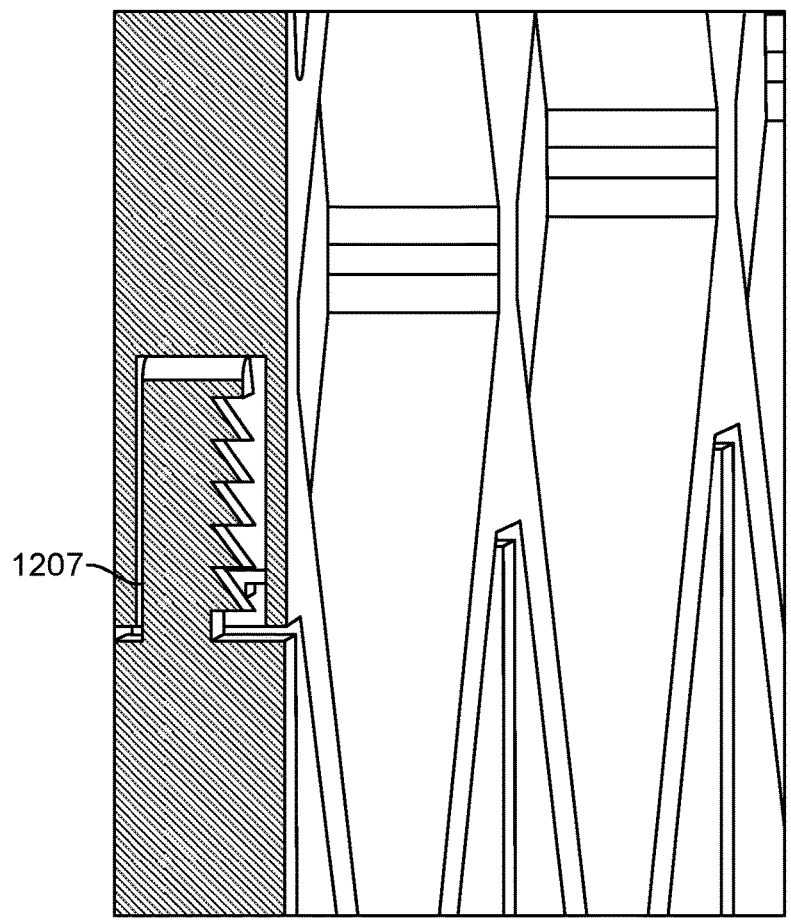
FIG. 12E is a magnified view of a ratchet in FIG. 12D.
Figure 12F:
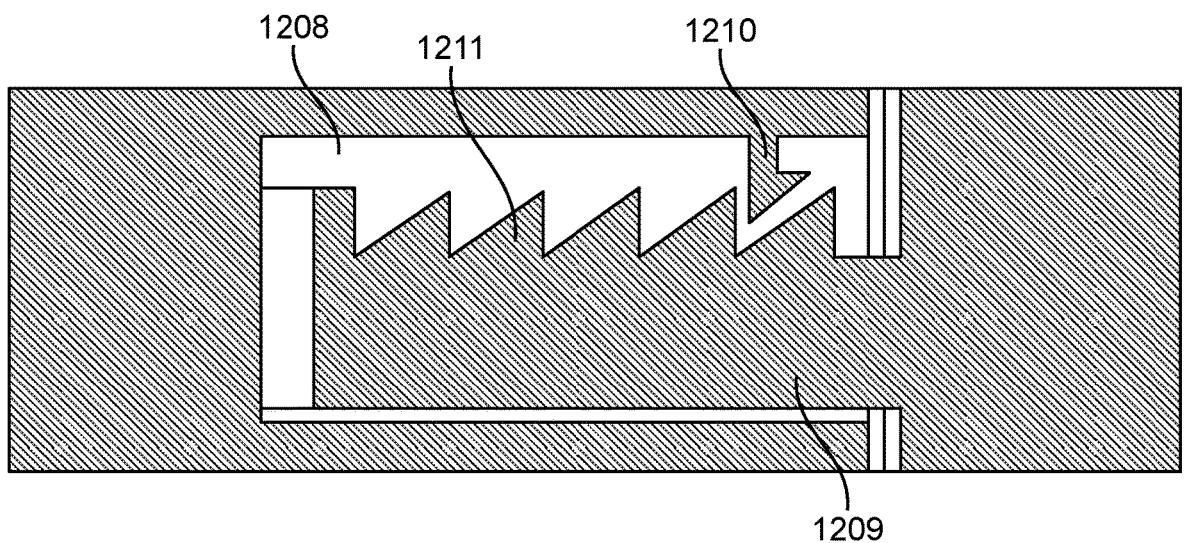
FIG. 12F is an alternative view of a ratchet in cross-section.

FIGS. 12A-12F illustrate an embodiment of a stent element having a ratcheting configuration. While FIGS. 12A-12F depict cells with diamond configurations, cells may have any closed cell configuration. FIG. 12A is a two-dimensional depiction of an element having a ratcheting configuration. FIG. 12B is a magnified view of the cells in FIG. 12A. FIG. 12C is an isometric view of the cells in FIG. 12A. FIG. 12D is a cross-sectional view of the cells in FIG. 12C showing the ratchet 1207. FIG. 12E is a magnified view of a ratchet 1207 in FIG. 12D. FIG. 12F is an alternative view of a ratchet 1207 in cross-section. A stent element with the cell structure of FIG. 12A would have a wrap orientation of left to right to form a cylinder. In this embodiment, element 1200 comprises intermixed ratcheting cells 1201 and non-ratcheting cells 1202. Ratcheting cells 1201 may be aligned in the longitudinal and/or the circumferential directions in a repeating pattern. Similarly, non-ratcheting cells 1202 may be aligned in the longitudinal and/or the circumferential directions in a repeating pattern. Additionally or alternatively, non-ratcheting cells 1202 and ratcheting cells 1201 may be helically aligned in an alternating pattern. In an embodiment, non-ratcheting 1202 and ratcheting cells 1201 are circumferentially offset. Additionally, non-ratcheting cells 1202 may be formed at a central location between four adjacent ratcheting cells 1201. In an embodiment illustrated in FIGS. 12A-12F, ratcheting cells 1201 may have the same or similar size as non-ratcheting cells 1202. Alternatively, ratcheting cells 1201 may be larger or smaller than non-ratcheting cells 1202. Adjacent longitudinally aligned ratcheting cells 1201 may be connected by longitudinal connecting struts 1205. Adjacent circumferentially aligned ratcheting cells 1201 may be connected by circumferential connecting struts 1206. In an embodiment, longitudinal connecting struts 1205 may have larger lengths or widths than circumferential connecting struts 1206. Alternatively, longitudinal connecting struts 1205 may have the same lengths or widths as circumferential connecting struts 1206. Ratcheting cells 1201 comprise longitudinally aligned ratcheting struts 1203. Longitudinally aligned corners of ratcheting cells 1201 and/or longitudinal connecting struts 1205 may comprise cavities 1208 to house linear racks 1209 on ratcheting struts 1203. Pawl 1210 engages teeth 1211 of linear rack 1209. Element 1200 may take a crimped form when mounted on an unexpanded balloon. Likewise, element 1200 may take an expanded form when expanded by a balloon. Linear rack 1207 moves in a longitudinal direction into cavity 1208 (depicted as down to up in FIG. 12E and right to left in FIG. 102) as the ratcheting element 1200 moves from a crimped state to an expanded state. Ratchet 1207 would thereby increase the radial strength of element 1200.

Figure 13A:
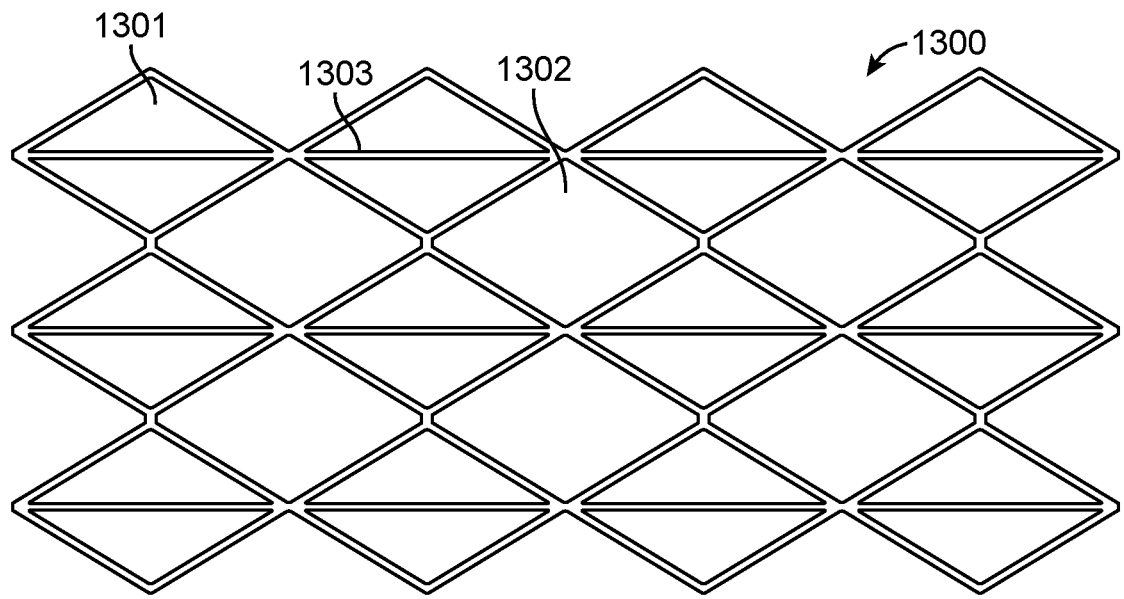
FIG. 13A is a two-dimensional depiction of an element having a bistable spring band configuration.
Figure 13B:
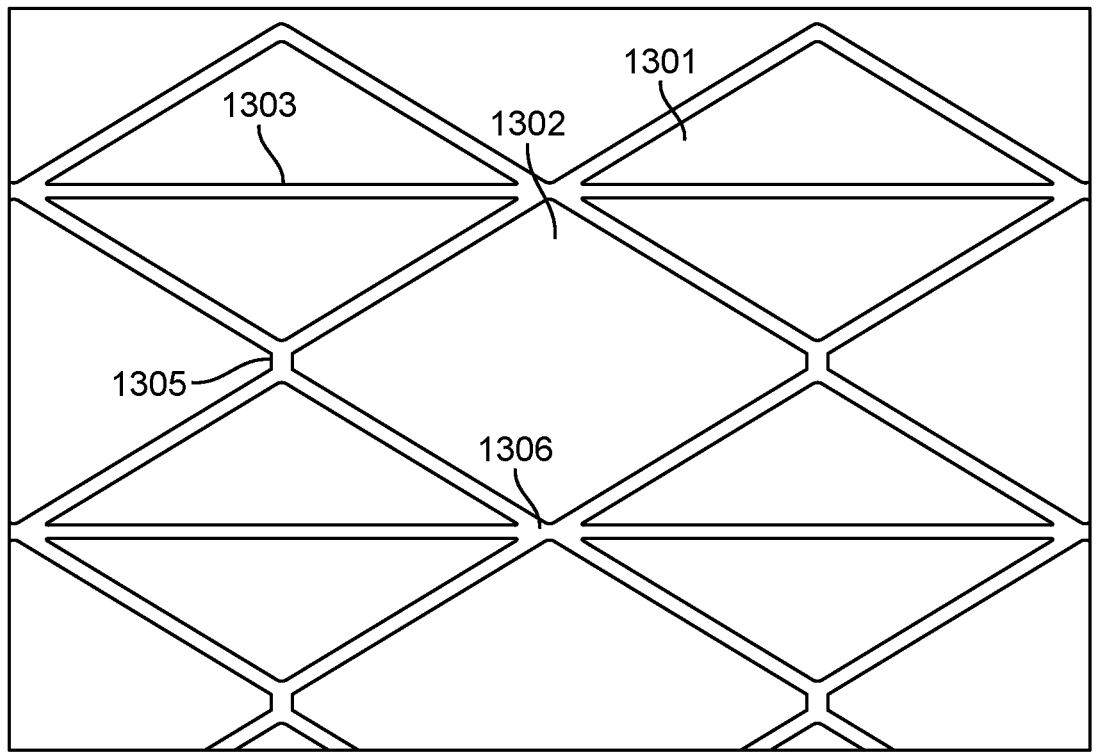
FIG. 13B is a magnified view of the cells in FIG. 13A.
Figure 13C:
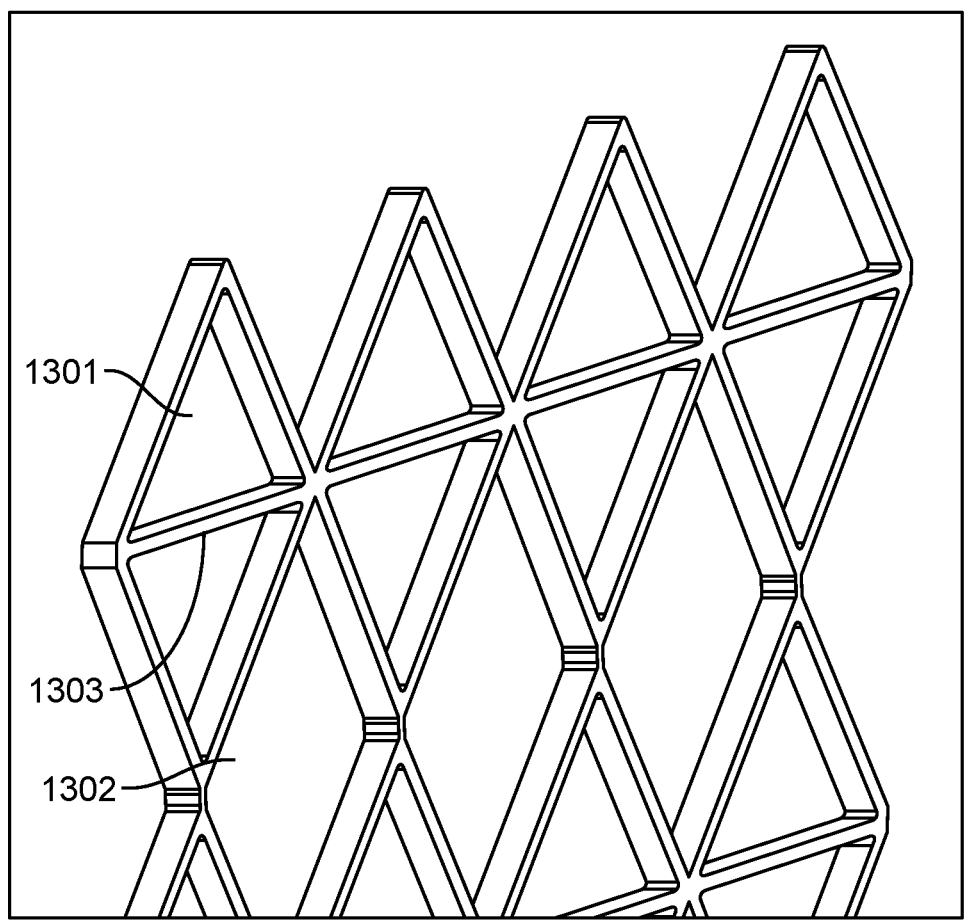
FIG. 13C is an isometric view of the cells in FIG. 13A.
Figure 13D:
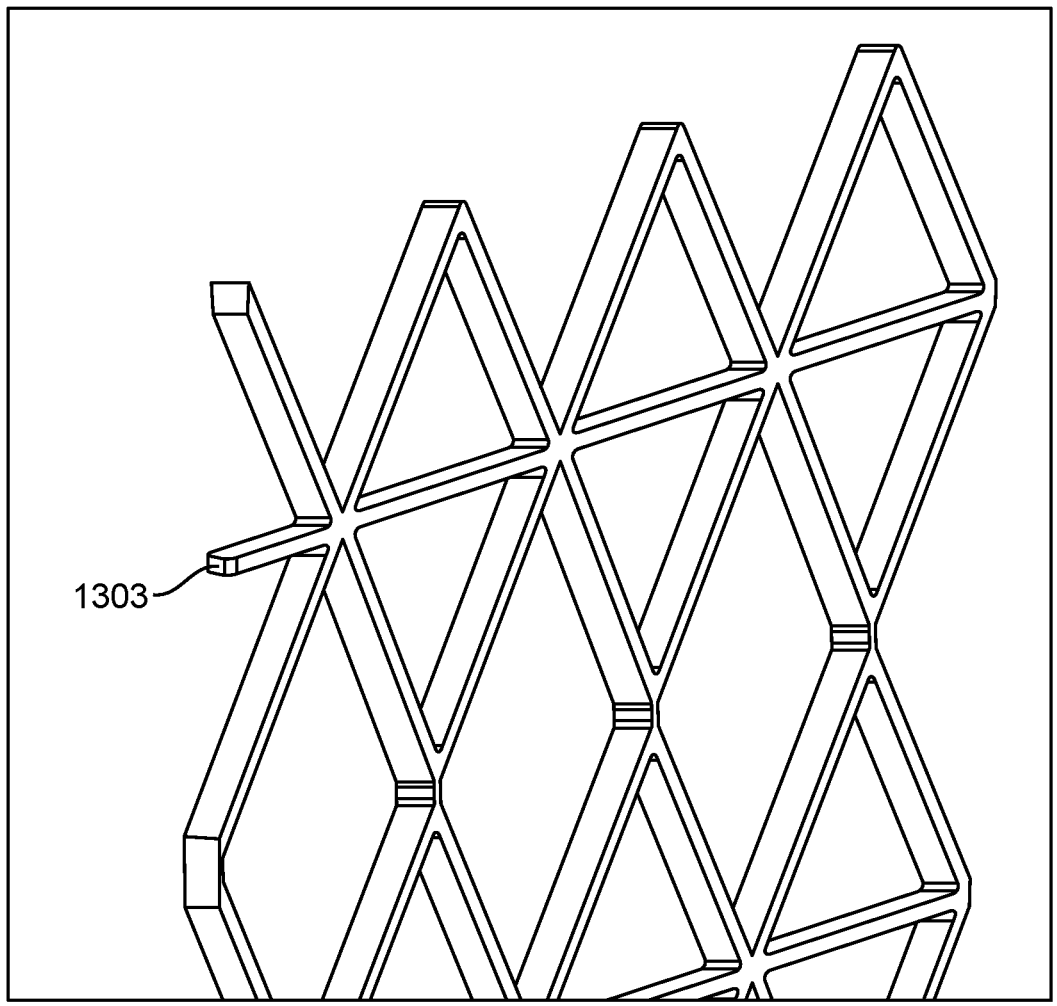
FIG. 13D is a cross-sectional view of the cells in FIG. 13C showing the curvature of bistable strut.
Figure 13E:
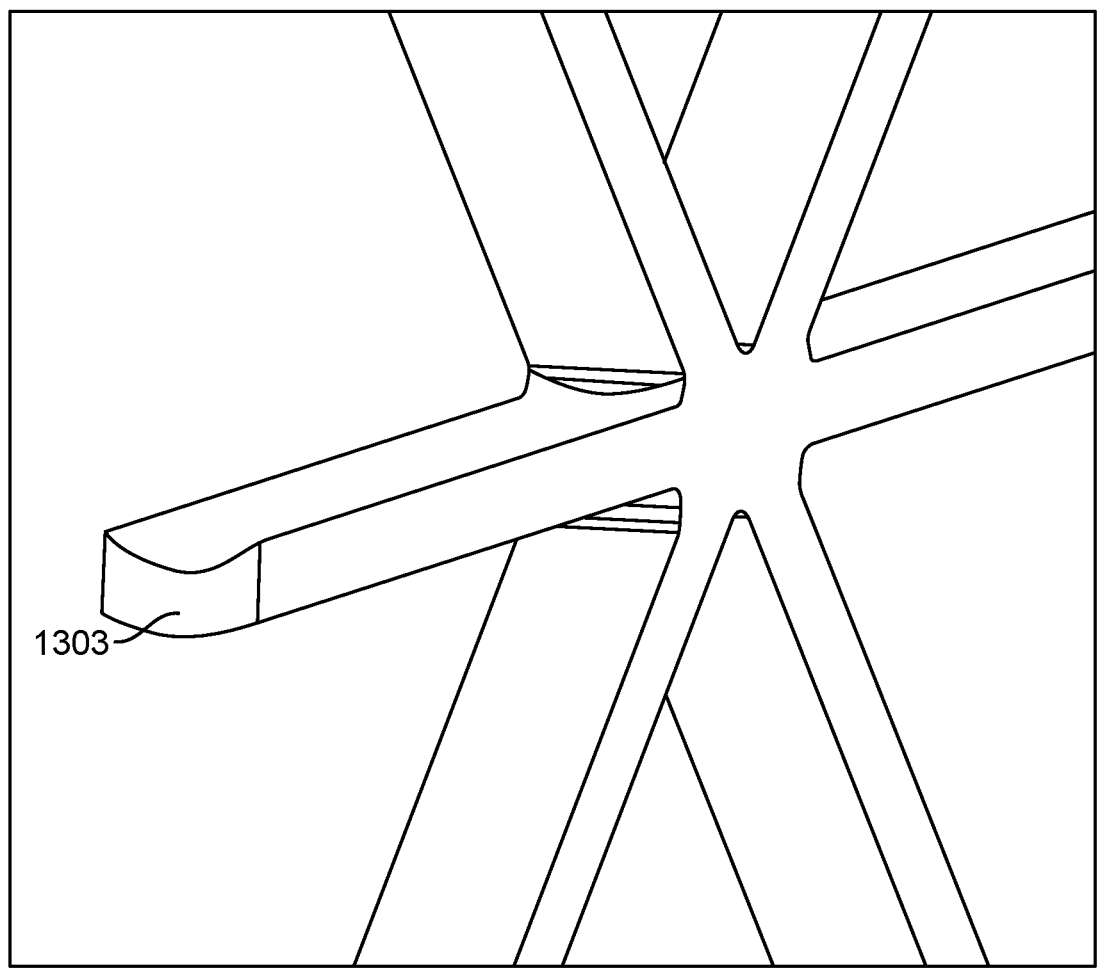
FIG. 13E is a magnified view of a bistable strut in FIG. 13D.
Figure 13F:
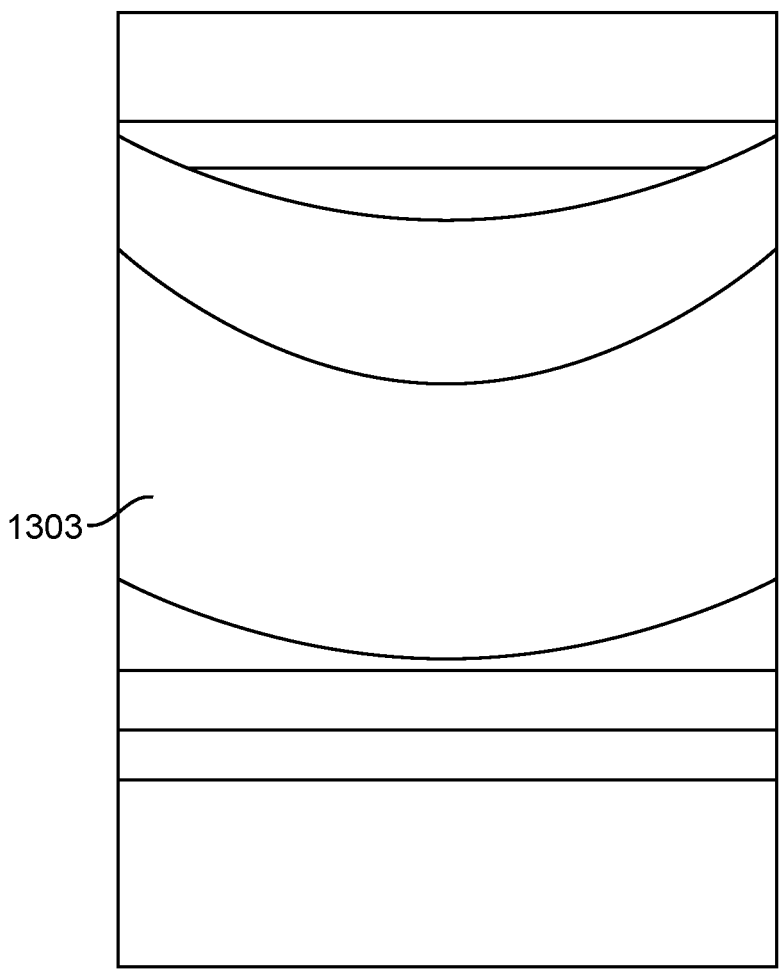
FIG. 13F is an alternative view of a bistable strut in cross-section.

FIGS. 13A-13F illustrate an embodiment of a stent element having a bistable spring band configuration. While FIGS. 13A-13F depict cells with diamond configurations, cells may have any closed cell configuration. FIG. 13A is a two-dimensional depiction of an element having a bistable spring band configuration. FIG. 13B is a magnified view of the cells in FIG. 13A. FIG. 13C is an isometric view of the cells in FIG. 13A. FIG. 13D is a cross-sectional view of the cells in FIG. 13C showing the curvature of bistable strut 1303. FIG. 13E is a magnified view of a bistable strut 1303 in FIG. 13D. FIG. 13F is an alternative view of a bistable strut 1303 in cross-section. A stent element with the cell structure of FIG. 13A would have a wrap orientation of left to right to form a cylinder. In this embodiment, element 1300 comprises intermixed bistable cells 1301 and non-bistable cells 1302. Bistable cells 1301 may be aligned in the longitudinal and/or the circumferential directions in a repeating pattern. Similarly, non-bistable cells 1302 may be aligned in the longitudinal and/or the circumferential directions in a repeating pattern. Additionally or alternatively, non-bistable cells 1302 and bistable cells 1301 may be helically aligned in an alternating pattern. In an embodiment, non-bistable 1302 and bistable cells 1301 are circumferentially offset. Additionally, non-bistable cells 1302 may be formed at a central location between four adjacent bistable cells 1301. In an embodiment illustrated in FIGS. 13A-13F, bistable cells 1301 may have the same or similar size as non-bistable cells 1302. Alternatively, bistable cells 1301 may be larger or smaller than non-bistable cells 1302. Adjacent longitudinally aligned bistable cells 1301 may be connected by longitudinal connecting struts 1305. Adjacent circumferentially aligned bistable cells 1301 may be connected by circumferential connecting struts 1306. In an embodiment, longitudinal connecting struts 1305 may have larger lengths or widths than circumferential connecting struts 1306. Alternatively, longitudinal connecting struts 1305 may have the same lengths or widths as circumferential connecting struts 1306. Bistable cells 1301 comprise circumferentially aligned bistable struts 1303. Bistable struts 1303 have a bistable spring band configuration. In an embodiment, bistable struts 1303 have a concavo-convex shape. Bistable struts 1303 may take a straight form or a bent form wherein the bistable strut 1303 bends in the concave direction. Rigidity of the bistable strut 1303 in the straight form increases radial strength of the element 1300. As depicted in FIGS. 13C-13F, the concave curve of bistable strut 1303 is oriented in the longitudinal direction and would face a proximal or distal opening of the cylindrical element 1300. Element 1300 may take a crimped form when mounted on an unexpanded balloon. Likewise, element 1300 may take an expanded form when expanded by a balloon. Bistable strut 1303 would have a bent configuration in the crimped form. In the expanded state, the bistable strut would have a straight configuration.

Figure 14A:
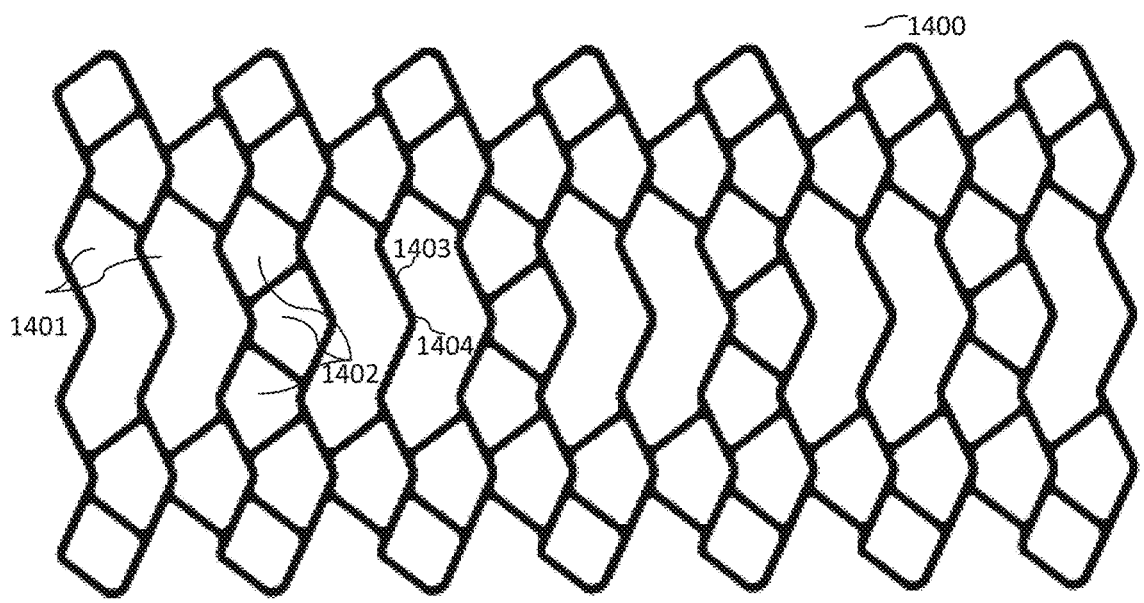
FIG. 14A is a two-dimensional depiction of an element having a pivoting configuration.
Figure 14B:
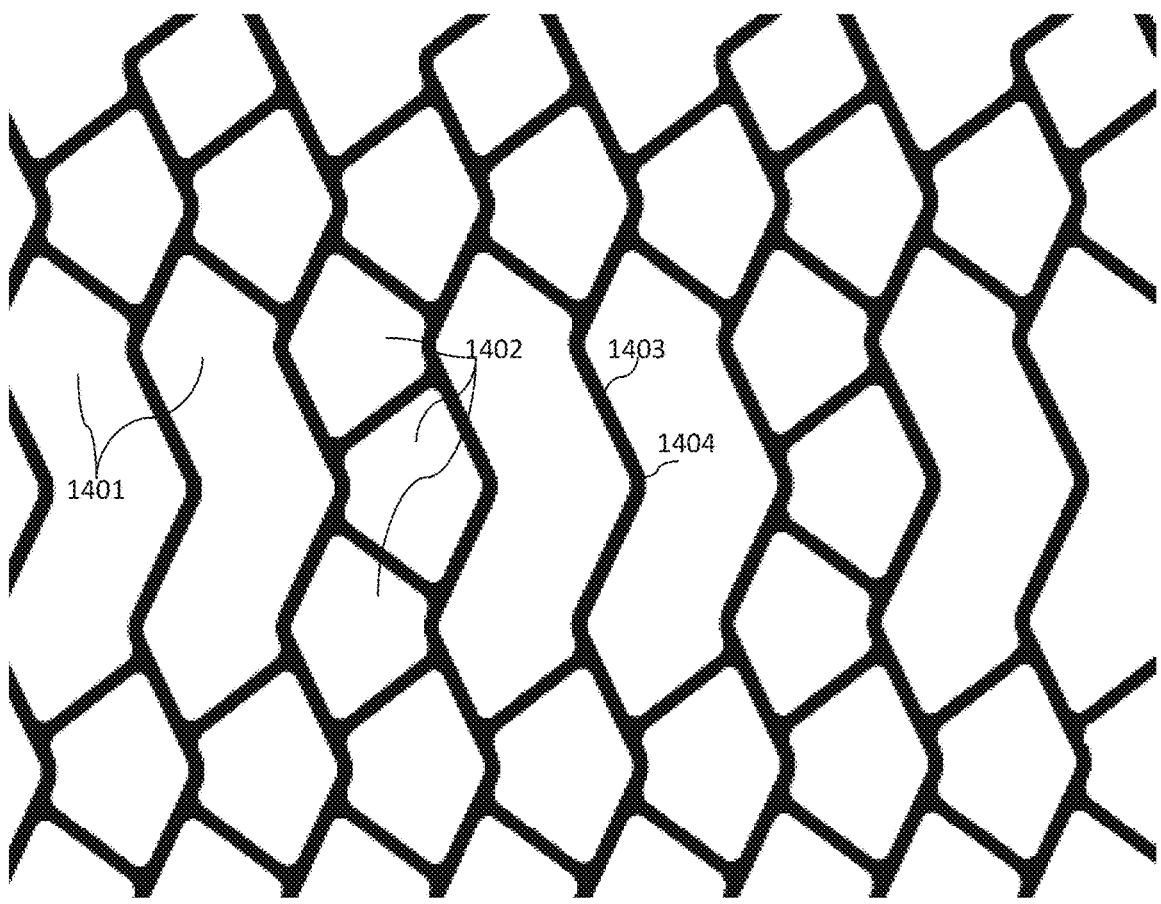
FIG. 14B is a magnified view of the cells in FIG. 14A.

FIGS. 14A-14B illustrate an embodiment of a stent element having a pivoting configuration. FIG. 14A is a two-dimensional depiction of an element having a pivoting configuration. FIG. 14B is a magnified view of the cells in FIG. 14A. A stent element with the cell structure of FIG. 14A would have a wrap orientation of left to right to form a cylinder. In this embodiment, element 1400 comprises an alternating sequence of 2 larger cells 1401 and a set of smaller cells 1402. The two larger cells 1401 allow bending of the free moving pivoting strut 1403 separating the two larger cells 1401. Element 1400 may take a crimped form when mounted on an unexpanded balloon. Likewise, element 1400 may take an expanded form when expanded by a balloon. FIGS. 14A-14B depict the pivoting strut 1403 in an unstable, less rigid configuration present when the element 1400 is in a crimped state. When expanded, the apex 1404 of the pivoting strut 1403 would shift from the right to the left (based on the orientation in FIG. 14A-14B), thereby increasing the rigidity of the pivoting strut 1403 and increasing the radial strength of the element 1400.

Figure 15A:
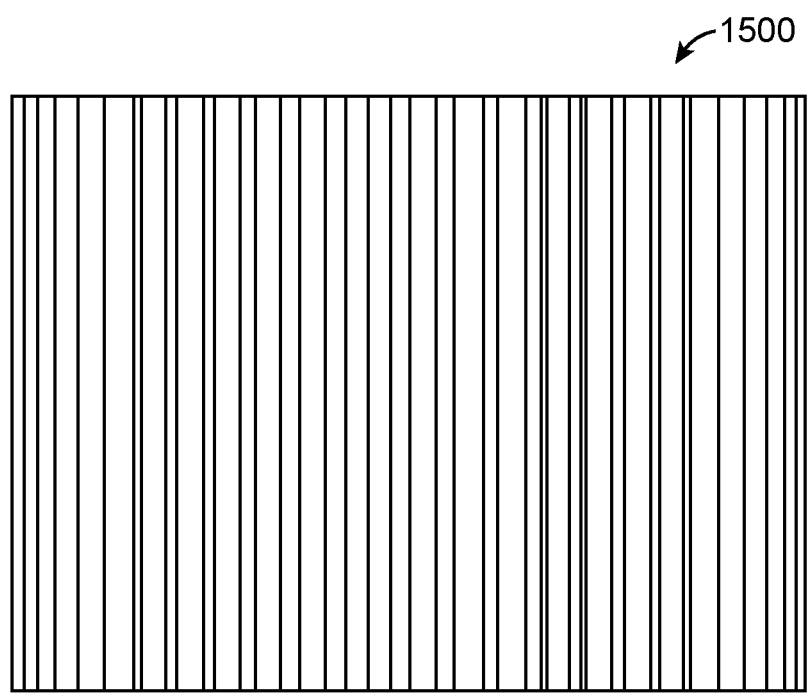
FIG. 15A is a side view of a cylindrical element having a corrugated or arch configuration.
Figure 15B:
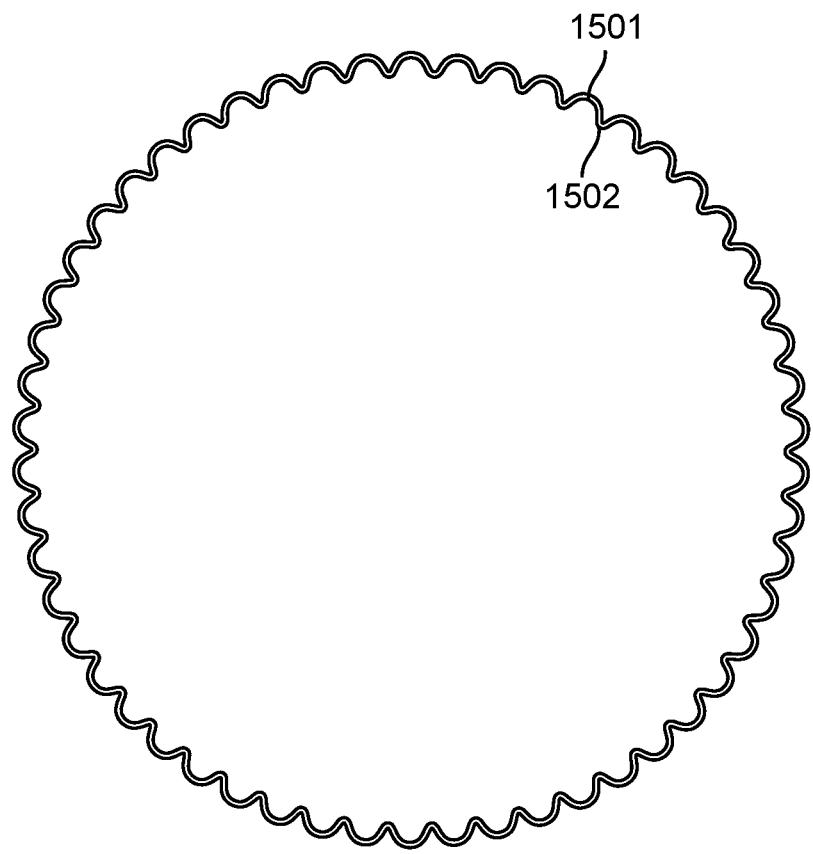
FIG. 15B is a top view of a corrugated element.
Figure 15C:
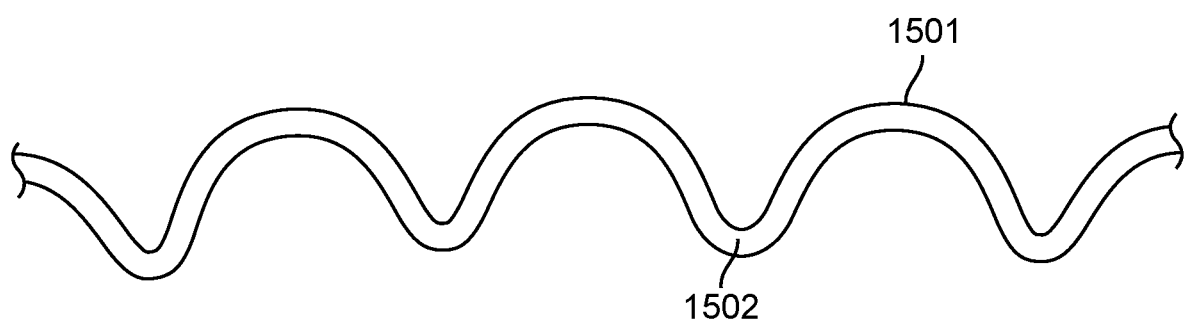
FIG. 15C is a magnified view of the element in FIG. 15B.
Figure 15D:
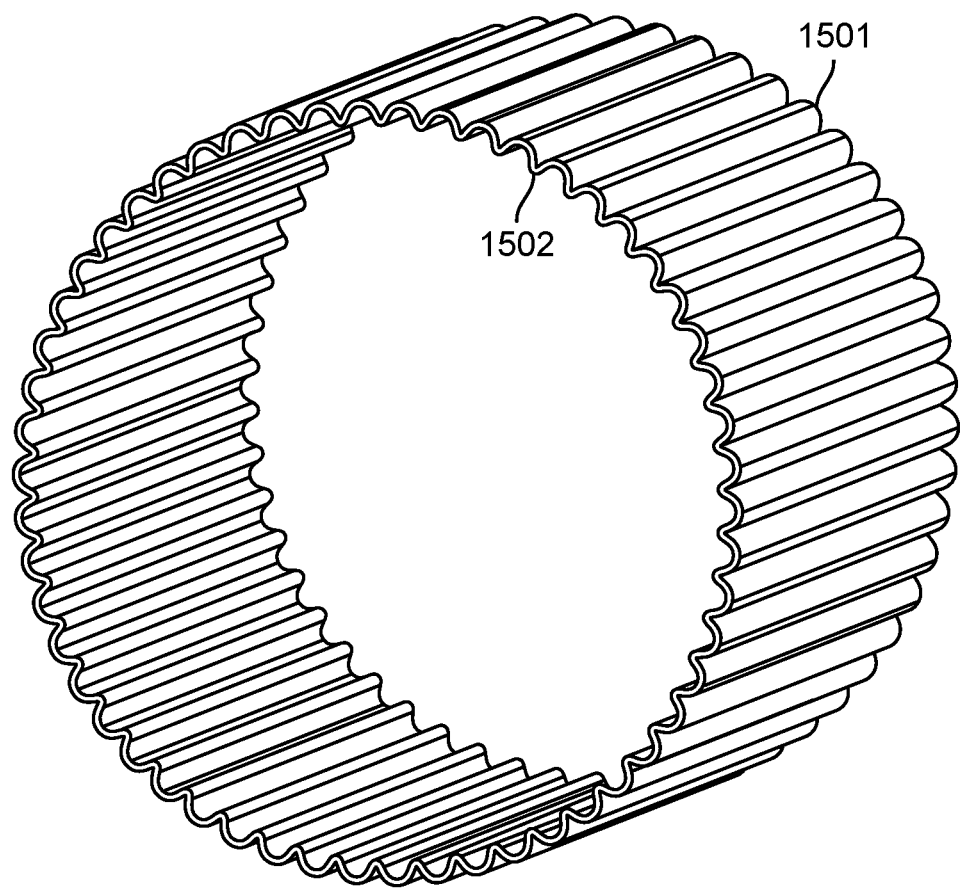
FIG. 15D is an isometric view of a cylindrical element having a corrugated configuration.
Figure 15E:
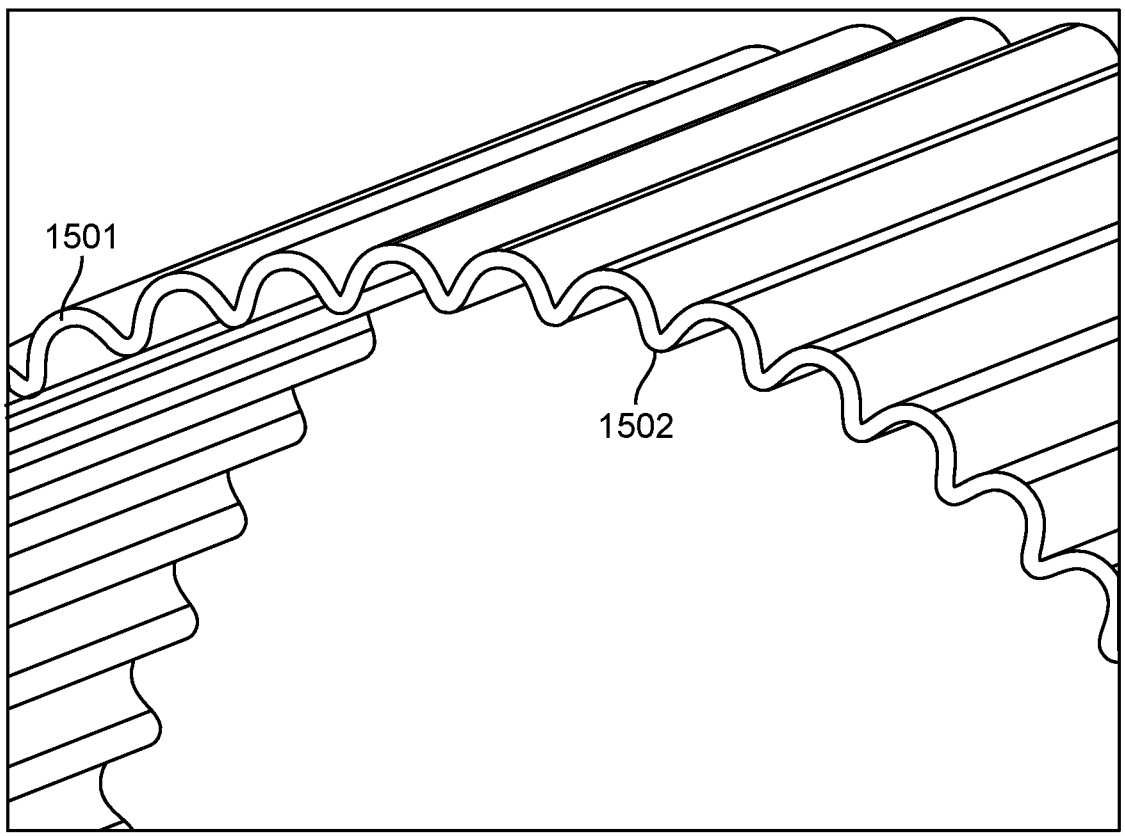
FIG. 15F a magnified view of the element in FIG. 15E.

FIGS. 15A-15F illustrate an embodiment of a stent element having a corrugated or arch configuration. FIG. 15A is a side view of a cylindrical element having a corrugated configuration. FIG. 15B is a top view of a corrugated element. FIG. 15C is a magnified view of the element in FIG. 15B. FIG. 15D is an isometric view of a cylindrical element having a corrugated configuration. FIG. 15F a magnified view of the element in FIG. 15E. Element 1500 comprises alternating convex ridges 1501 and concave grooves 1502. In an embodiment, as depicted in FIGS. 15A, 15D, and 15E, element 1500 may comprise solid walls. In an embodiment, corrugated element 1500 may have a longitudinal length of approximately 3 mm. Alternatively, corrugated elements may have longitudinal lengths of 1-2 mm. Short longitudinal lengths allow stent elements 1500 to be placed with solid walls. In another embodiment, corrugated element 1500 may have cell patterns cut into the corrugated cylinder. Alternatively, element 1500 may be manufactured with arches, ridges, and cell patterns using an additive manufacturing process. Element 1500 may take a crimped form when mounted on an unexpanded balloon. Likewise, element 1500 may take an expanded form when expanded by a balloon. As the corrugated cell 1500 moves from a crimped state to an expanded state, ridges 1501 and/or valleys 1502 will widen.

Any suitable therapeutic agent (or "drug") may be incorporated into, coated on, or otherwise attached to the stent, in various embodiments. Examples of such therapeutic agents include, but are not limited to, antithrombotics, anticoagulants, antiplatelet agents, anti-lipid agents, thrombolytics, antiproliferatives, anti-inflammatories, agents that inhibit hyperplasia, smooth muscle cell inhibitors, antibiotics, growth factor inhibitors, cell adhesion inhibitors, cell adhesion promoters, antimitotics, antifibrins, antioxidants, anti-neoplastics, agents that promote endothelial cell recovery, matrix metalloproteinase inhibitors, anti-metabolites, antiallergic substances, viral vectors, nucleic acids, monoclonal antibodies, inhibitors of tyrosine kinase, antisense compounds, oligonucleotides, cell permeation enhancers, hypoglycemic agents, hypolipidemic agents, proteins, nucleic acids, agents useful for erythropoiesis stimulation, angiogenesis agents, anti-ulcer/anti-reflux agents, and anti-nauseants/anti-emetics, PPAR alpha agonists such as fenofibrate, PPAR-gamma agonists selected such as rosiglitazaone and pioglitazone, sodium heparin, LMW heparins, heparoids, hirudin, argatroban, forskolin, vapriprost, prostacyclin and prostacylin analogues, dextran, D-phe-pro-arg-chloromethylketone (synthetic anti-thrombin), glycoprotein IIb/IIIa (platelet membrane receptor antagonist antibody), recombinant hirudin, thrombin inhibitors, indomethacin, phenyl salicylate, beta-estradiol, vinblastine, ABT-627 (astrasentan), testosterone, progesterone, paclitaxel, methotrexate, fotemusine, RPR-101511A, cyclosporine A, vincristine, carvediol, vindesine, dipyridamole, methotrexate, folic acid, thrombospondin mimetics, estradiol, dexamethasone, metrizamide, iopamidol, iohexol, iopromide, iobitridol, iomeprol, iopentol, ioversol, ioxilan, iodixanol, and iotrolan, antisense compounds, inhibitors of smooth muscle cell proliferation, lipid-lowering agents, radiopaque agents, antineoplastics, HMG CoA reductase inhibitors such as lovastatin, atorvastatin, simvastatin, pravastatin, cerivastatin and fluvastatin, and combinations thereof.

Examples of antithrombotics, anticoagulants, antiplatelet agents, and thrombolytics include, but are not limited to, sodium heparin, unfractionated heparin, low molecular weight heparins, such as dalteparin, enoxaparin, nadroparin, reviparin, ardoparin and certaparin, heparinoids, hirudin, argatroban, forskolin, vapriprost, prostacyclin and prostacylin analogues, dextran, D-phe-pro-arg-chloromethylketone (synthetic antithrombin), dipyridamole, glycoprotein IIb/IIIa (platelet membrane receptor antagonist antibody), recombinant hirudin, and thrombin inhibitors such as bivalirudin, thrombin inhibitors, and thrombolytic agents, such as urokinase, recombinant urokinase, pro-urokinase, tissue plasminogen activator, ateplase and tenecteplase.

Examples of cytostatic or antiproliferative agents include, but are not limited to, rapamycin and its analogs, including everolimus, zotarolimus, tacrolimus, novolimus, and pimecrolimus, angiopeptin, angiotensin converting enzyme inhibitors, such as captopril, cilazapril or lisinopril, calcium channel blockers, such as nifedipine, amlodipine, cilnidipine, lercanidipine, benidipine, trifluperazine, diltiazem and verapamil, fibroblast growth factor antagonists, fish oil (omega 3-fatty acid), histamine antagonists, lovastatin, topoisomerase inhibitors, such as etoposide and topotecan, as well as antiestrogens such as tamoxifen.

Examples of anti-inflammatory agents include, but are not limited to, colchicine and glucocorticoids, such as betamethasone, cortisone, dexamethasone, budesonide, prednisolone, methylprednisolone and hydrocortisone. Non-steroidal anti-inflammatory agents include, but are not limited to, flurbiprofen, ibuprofen, ketoprofen, fenoprofen, naproxen, diclofenac, diflunisal, acetominophen, indomethacin, sulindac, etodolac, diclofenac, ketorolac, meclofenamic acid, piroxicam and phenylbutazone.

Examples of antineoplastic agents include, but are not limited to, alkylating agents including altretamine, bendamucine, carboplatin, carmustine, cisplatin, cyclophosphamide, fotemustine, ifosfamide, lomustine, nimustine, prednimustine, and treosulfin, antimitotics, including vincristine, vinblastine, paclitaxel, docetaxel, antimetabolites including methotrexate, mercaptopurine, pentostatin, trimetrexate, gemcitabine, azathioprine, and fluorouracil, antibiotics, such as doxorubicin hydrochloride and mitomycin, and agents that promote endothelial cell recovery such as estradiol.

Antiallergic agents include, but are not limited to, permirolast potassium nitroprusside, phosphodiesterase inhibitors, prostaglandin inhibitors, suramin, serotonin blockers, steroids, thioprotease inhibitors, triazolopyrimidine, and nitric oxide.

The beneficial agent may include a solvent. The solvent may be any single solvent or a combination of solvents. For purpose of illustration and not limitation, examples of suitable solvents include water, aliphatic hydrocarbons, aromatic hydrocarbons, alcohols, ketones, dimethyl sulfoxide, tetrahydrofuran, dihydrofuran, dimethylacetamide, acetates, and combinations thereof.

Stents may be manufactured using an additive or a subtractive. In any of the described embodiments, stents or stent elements may be manufactured as a sheet and wrapped into cylindrical form. Alternatively, stents or stent elements may be manufactured in cylindrical form using an additive manufacturing process. In an embodiment, stents maybe formed by extruding a material into a cylindrical tubing. In some embodiments, a longer stent element, may be formed during the manufacturing process and then cut into smaller stent elements/elements to provide a multi-element stent. In an embodiment, stent tubing may be laser cut with a pattern to form a stent element.

Figure 16:
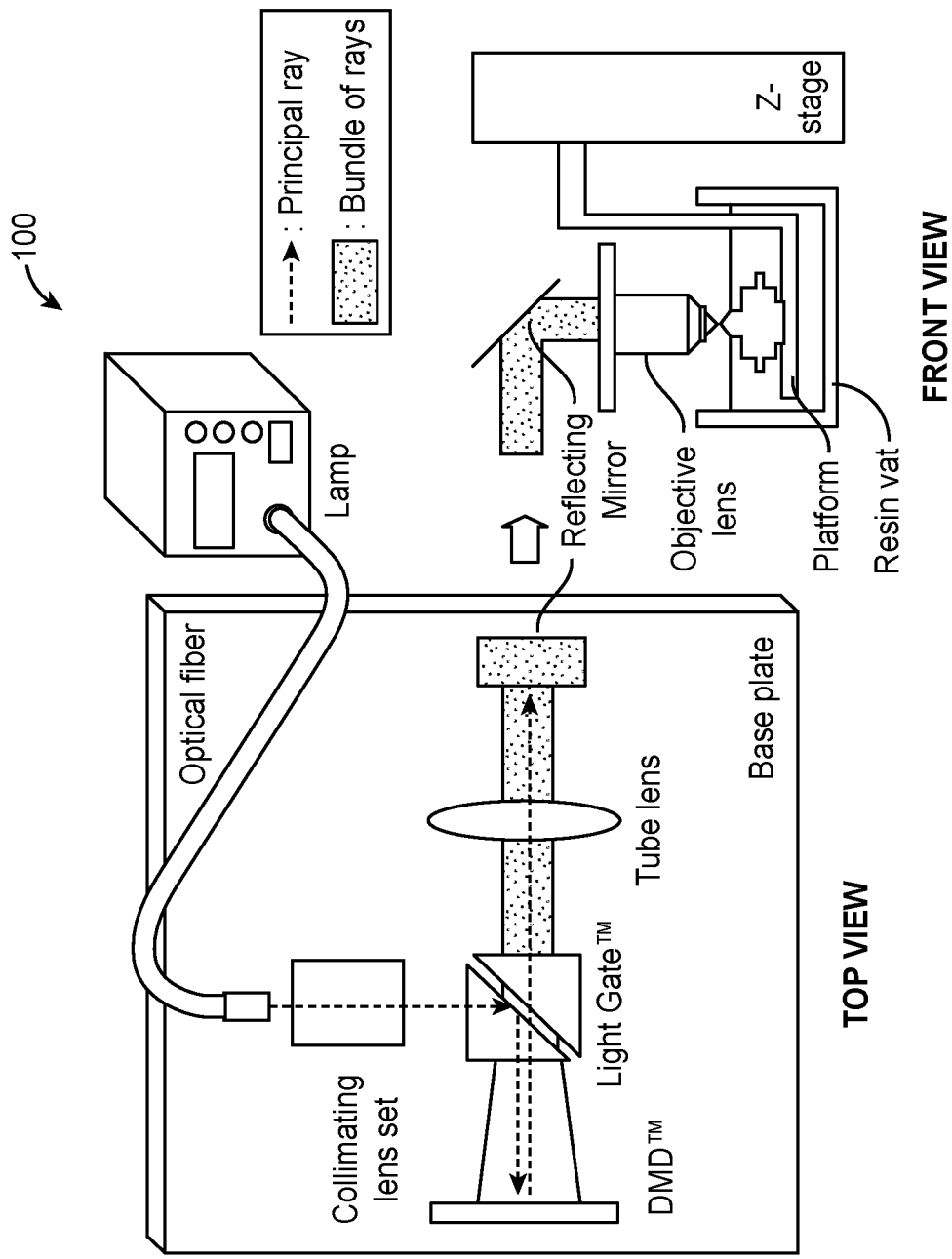
FIG. 16 is a schematic diagram of a micro-stereolithograph used to create a stent, according to one embodiment.

Referring now to FIG. 16, in one embodiment, stents may be manufactured using a micro-stereolithography system 100 (or "3D printing system"). Several examples of currently available systems that might be used in various embodiments include, but are not limited to: MakiBox A6, Makible Limited, Hong Kong; CubeX, 3D Systems, Inc., Circle Rock Hill, S.C.; and 3D-Bioplotter, (EnvisionTEC GmbH, Gladbeck, Germany).

The micro-stereolithography system may include an illuminator, a dynamic pattern generator, an image-former and a Z-stage. The illuminator may include a light source, a filter, an electric shutter, a collimating lens and a reflecting mirror that projects a uniformly intense light on a digital mirror device (DMD), which generates a dynamic mask. FIG. 7 shows some of these components of one embodiment of the micro-stereolithography system 100, including a DMD board, Z-stage, lamp, platform, resin vat and an objective lens. The details of 3D printing/micro-stereolithography systems and other additive manufacturing systems will not be described here, since they are well known in the art. However, according to various embodiments, any additive manufacturing system or process, whether currently known or hereafter developed, may potentially be used to fabricate stents within the scope of the present invention. In other words, the scope of the invention is not limited to any particular additive manufacturing system or process.

In one embodiment, the system 100 may be configured to fabricate stents using dynamic mask projection micro-stereolithography. In one embodiment, the fabrication method may include first producing 3D microstructural scaffolds by slicing a 3D model with a computer program and solidifying and stacking images layer by layer in the system. In one embodiment, the reflecting mirror of the system is used to project a uniformly intense light on the DMD, which generates a dynamic mask. The dynamic pattern generator creates an image of the sliced section of the fabrication model by producing a black-and-white region similar to the mask. Finally, to stack the images, a resolution Z-stage moves up and down to refresh the resin surface for the next curing. The Z-stage build subsystem, in one embodiment, has a resolution of about 100 nm and includes a platform for attaching a substrate, a vat for containing the polymer liquid solution, and a hot plate for controlling the temperature of the solution. The Z-stage makes a new solution surface with the desired layer thickness by moving downward deeply, moving upward to the predetermined position, and then waiting for a certain time for the solution to be evenly distributed.

Although particular embodiments have been shown and described, they are not intended to limit the invention. Various changes and modifications may be made to any of the embodiments, without departing from the spirit and scope of the invention. The invention is intended to cover alternatives, modifications, and equivalents.

What is claimed is:

1. A method for manufacturing an intravascular stent comprising:
    loading a multi-element stent comprising multiple individual stent elements onto an inflatable balloon such that the stent elements are positioned serially along a longitudinal length of the balloon and the stent elements do not touch one another, wherein the stent elements are spaced such that after implantation the stent elements do not touch one another at a target vessel location during skeletal movement;
    wherein the distance between each stent element is based on a diameter (D) of the stent element in an expanded state at a target vessel location and an angle (θ) created between stent elements during maximal flexion of the target vessel location during skeletal movement;
    wherein the stent is configured to be radially rigid and longitudinally flexible after implantation at the target vessel location; and
    wherein the distance between each stent element is greater than or equal to $$\sqrt{\frac{D^2}{2}(1-\cos\theta)}.$$

2. The method of claim 1, wherein the distance between each stent element is further based on a length of the stent elements, wherein the distance between each stent element increases with increased length of the stent elements.

3. The method of claim 1, wherein the distance between each stent element is further based on a number of elements in the multi-element stent, wherein the distance between each stent element decreases with increased number of elements in the multi-element stent.

4. The method of claim 1, wherein the distance between each stent element is further based on a maximum percent axial compression of the stent elements at the target vessel location, wherein the distance between each stent element increases with an increase of the maximum percent axial compression of the stent elements at the target vessel location.

5. The method of claim 1, wherein the stent elements are equal in length.

6. The method of claim 1, wherein the multi-element stent is comprised of more than two stent elements, and wherein the distances between each stent element are equal.

7. The method of claim 1, wherein each of the stent elements are separated by a distance of at least half a millimeter while mounted on the balloon and after implantation.

8. The method of claim 1, wherein the stent is formed from a material comprising poly(L-lactic acid) (PLLA), poly(D-lactic acid) (PDLA), poly(D,L-lactic acid) (PDLLA), semi crystalline polylactide, polyglycolic acid (PGA), poly(lactic-co-glycolic acid) (PLGA), poly(iodinated desamino tyrosyl-tyrosine ethyl ester) carbonate, polycaprolactone (PCL), salicylate based polymer, polydioxanone (PDS), poly(hydroxybutyrate), poly(hydroxybutyrate-co-valerate), polyorthoester, polyanhydride, poly(glycolic acid-co-trimethylene carbonate), poly(iodinated desaminotyrosyl-tyrosine ethyl ester) carbonate, polyphosphoester, polyphosphoester urethane, poly(amino acids), cyanoacrylates, poly(trimethylene carbonate), poly(iminocarbonate), polyalkylene oxalates, polyphosphazenes, polyiminocarbonates, and aliphatic polycarbonates, fibrin, fibrinogen, cellulose, starch, collagen, polyurethane including polycarbonate urethanes, polyethylene, polyethylene terephthalate, ethylene vinyl acetate, ethylene vinyl alcohol, silicone including polysiloxanes and substituted polysiloxanes, polyethylene oxide, polybutylene terephthalate-co-PEG, PCL-co-PEG, PLA-co-PEG, PLLA-co-PCL, polyacrylates, polyvinyl pyrrolidone, polyacrylamide, or combinations thereof.

9. The method of claim 8, wherein the material is extruded into a cylindrical tubing.

10. The method of claim 1, wherein the stent elements are coated with an anti-proliferative agent.

11. The method of claim 1, wherein the stent elements comprise a plurality of diamond shaped closed cells longer in a radial direction than in a longitudinal direction in the expanded state.

12. The method of claim 1, wherein the distance between each stent element in an unexpanded state is less than or equal to the distance between each stent element in the expanded state.

* * * * *